United States Patent
Cole et al.

[11] Patent Number: 5,989,222
[45] Date of Patent: Nov. 23, 1999

[54] PRESSURE (OCCLUSION) SENSOR

[75] Inventors: Martin A. Cole, San Diego; Michael W. Lawless; Christopher D. Lynch, both of Poway; Frank S. C. Mo, Santa Clara; Peter A. Soberon, San Diego, all of Calif.

[73] Assignee: Abbott Laboratories, Abbott Park, Ill.

[21] Appl. No.: 09/097,062

[22] Filed: Jun. 12, 1998

[51] Int. Cl.⁶ .................................................. A61M 1/100
[52] U.S. Cl. .......................................................... 604/151
[58] Field of Search ................................... 604/151, 152, 604/65, 66, 67; 128/DIG. 13

[56] References Cited

U.S. PATENT DOCUMENTS

| | | | |
|---|---|---|---|
| 554,115 | 9/1896 | Thomas et al. | 604/67 |
| 4,690,673 | 9/1987 | Bloomquist | 128/DIG. 13 |
| 4,784,576 | 11/1988 | Bloom et al. | 604/65 |
| 5,213,573 | 5/1993 | Sorich et al. | 604/66 |
| 5,695,473 | 12/1997 | Olsen | 128/DIG. 13 |

FOREIGN PATENT DOCUMENTS

| | | | |
|---|---|---|---|
| 8400690 | 3/1984 | WIPO | 604/151 |

*Primary Examiner*—Jeffrey A. Smith
*Assistant Examiner*—Eduando C. Robert
*Attorney, Agent, or Firm*—Neal D. Marcus

[57] ABSTRACT

A system and a method for detecting the presence of an occlusion in an intravenous (IV) line supplying a medicinal liquid to a patient. Two pressure occlusion sensors are employed to produce a value for the proximal and distal pressures within an IV pumping cassette that is disposed in the fluid path of the IV line. Each pressure occlusion sensor includes a strain gauge connected to a leaf spring that is fixed at one end within a pump chassis and a rod that is disposed transverse to the leaf spring. Each rod has one end that responds to the force of a portion of an elastomeric membrane inside the pumping cassette and another end that contacts a free end of the leaf spring. When a leaf spring is flexed by the movement of a rod, the strain gauge mounted on the leaf spring produces a differential voltage that corresponds to a fluid pressure within the pumping cassette. The distal pressure occlusion sensor automatically opens a flow stop on the pumping cassette when the pumping cassette is inserted into the pump chassis. The outputs from the distal and proximal pressure sensors are sampled at least once per second to ensure that maximum pressure values are not exceeded and that a pressure sensor failure is immediately detected.

33 Claims, 18 Drawing Sheets

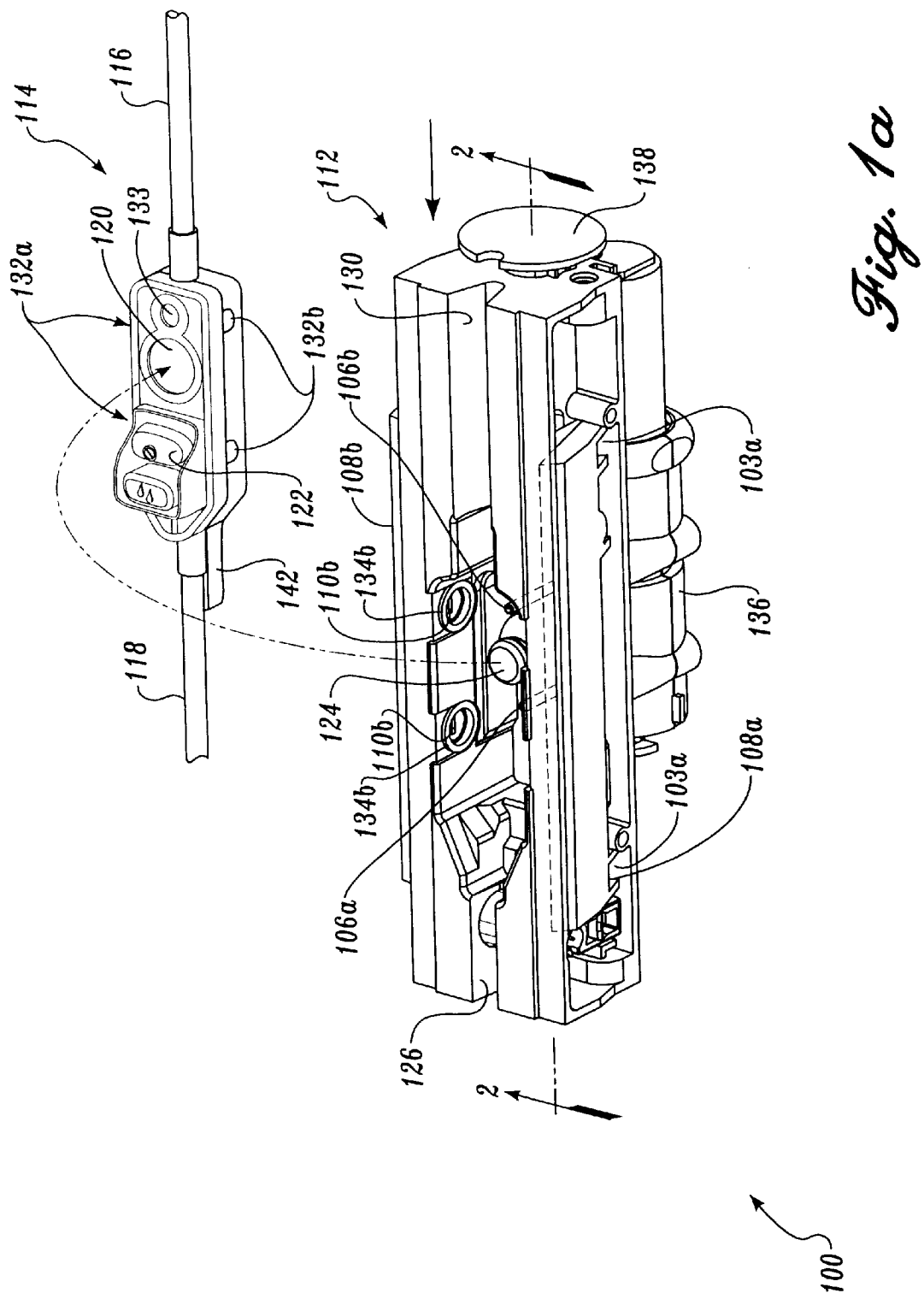

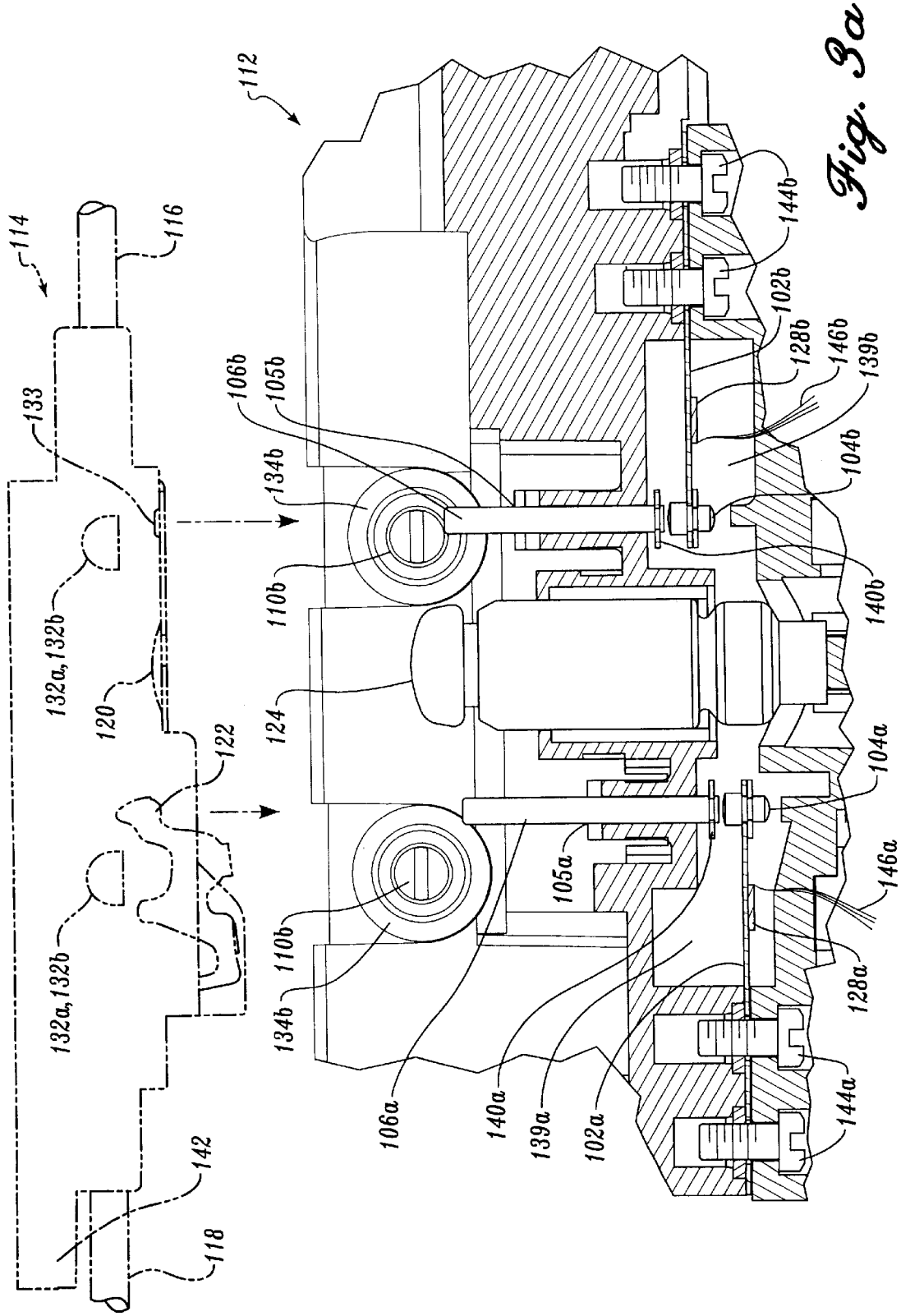

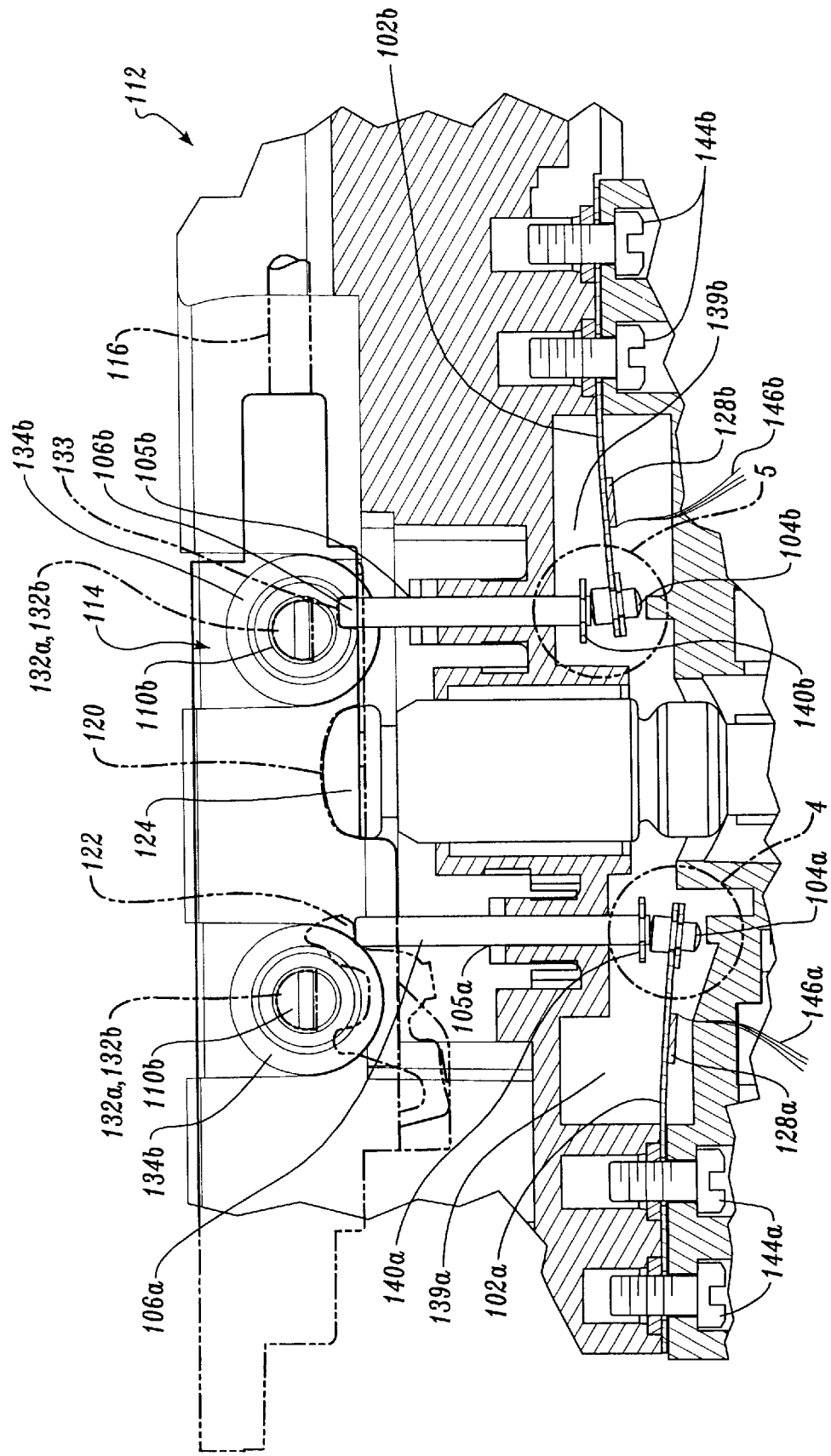

203
THRESHOLD_ADC = THRESHOLD_ADC_AT_CALIBRATION + BASELINE_ADC - FACTORY_ZERO_PSI

205
THRESHOLD_ADC = GAIN * PSI + BASELINE_ADC

207
DELTA_COUNTS = GAIN * DELTA_PSI

209
RELATIVE_ADC = FACTORY_GAIN * RELATIVE_PSI + BASELINE_ADC

211
ADC = FACTORY_GAIN * PSI + FACTORY_ZERO_PSI

PRESSURE (OCCLUSION) SENSOR

FIELD OF THE INVENTION

The present invention relates generally to sensing an occlusion affecting fluid flow in an intravenous line, and more particularly, to the use of a pressure sensor for determining an occlusion of an intravenous line coupled to a fluid pump.

BACKGROUND OF THE INVENTION

Intravenous (IV) lines are used to convey medicinal fluids into a patient's cardiovascular system. A typical IV line includes a fluid reservoir coupled to one end of a flexible tubing that is connected in fluid communication with a large vein of a patient. An inline IV pump is often employed to effect and control the flow of the medicinal fluid through the tubing to the patient. Also, at least one occlusion sensor is usually included to detect when the flow of fluid through the IV line is fully or partially interrupted. Partial or complete occlusion of fluid flow is one of the more common problems in the use of an IV line. The patient may unintentionally compress the tubing, e.g., by rolling onto it, and stop the fluid flow, or a blood clot may block the flow of fluid where it enters the cardiovascular system. In addition, an electrical or mechanical failure of an IV pump disposed in the IV line may cause the flow of fluid through the line to be impeded. Problems can also arise if false alarms are triggered by minor pumping irregularities or occasional spikes in the signal produced by the occlusion sensor, since too many false alarms can cause medical personnel to ignore valid alarms.

In the prior art, pressure activated occlusion sensors have been disposed at the proximal and distal ends of a disposable pumping cassette (IV pump) for determining when the flow of fluid through the IV line is impeded. When the measured pressures indicate that the flow of fluid is impeded, an alarm is activated that notifies medical personnel of the condition. Typically, a separate assembly is employed for coupling a pressure occlusion sensor to an IV line, and the occlusion sensor is disposed adjacent to an IV pump. However, the limited space adjacent to ambulatory IV pumps has generally restricted the use of pressure occlusion sensors to non-ambulatory IV pumps.

Prior art pressure occlusion sensors typically must be calibrated by medical personnel each time they are coupled to an IV line, using a time consuming procedure. Also, special training is often necessary for medical personnel to be proficient at calibrating the pressure occlusion sensors. Thus, a clear need has developed for a pressure occlusion sensor that is integrated with the IV pump to conserve space and which is automated to implement the calibration procedure. While accurately detecting any significant hindrance to fluid flow, such an occlusion sensor should minimize false alarms.

SUMMARY OF THE INVENTION

In accord with the present invention, an occlusion detector disposed in a pump that infuses a medicinal fluid into a patient through an intravenous line is defined. The occlusion detector determines if an impediment to fluid flow through the intravenous line has occurred. A beam that is cantilever mounted to the pump is included in the occlusion detector. This mounting configuration enables a free end of the beam to flex in response to a force applied to the free end of the beam. A strain gauge is mounted on the beam so as to sense a deflection of the beam. An elongate rod is disposed within an orifice formed within the pump and is movable in a direction aligned with a longitudinal axis of the rod. One end of the rod contacts the free end of the beam, and an opposite end of the rod experiences a force corresponding to a fluid pressure within the intravenous line, directed along the longitudinal axis of the rod. This force causes the beam to deflect and as a result, the strain gauge produces a signal indicative of the fluid pressure. An alarm is provided to indicate an impediment to fluid flow through the intravenous line. Coupled to the strain gauge to receive the signal is a controller. The controller samples the signal and determines a baseline pressure while the pump is operating. As a function of the baseline pressure, the controller determines a relative pressure. An impediment to the fluid flow through the intravenous line is detected by the controller as a function of the relative pressure and if such an impediment is detected, the controller activates the alarm to alert a user.

The baseline pressure is preferably reset each time the pump is energized and is determined by averaging a plurality of samples that do not differ from each other by more than a predetermined amount. In addition, the baseline pressure is limited to the greater of a predefined function of a maximum sample, and a predetermined value. As another aspect of the invention, the baseline pressure is limited to the lesser of a predefined function of a minimum sample, and a predetermined value.

The controller also detects an impediment to the fluid flow as a function of an absolute pressure derived from the samples and independent of the baseline pressure. Preferably, the signal produced by the strain gauge is indicative of either a distal pressure or a proximal pressure in the intravenous line.

The rod is fabricated of a material selected for its low coefficient of friction, to minimize friction between the rod and sides of the orifice. Further, the free end of the beam includes a knob disposed adjacent to and in contact with the end of the rod. Either the end of the rod or a surface of the knob in contact with the end of the rod is rounded to minimize application of a force on the beam that is not aligned with the longitudinal axis of the rod. The other end of the rod preferably contacts an elastomeric membrane disposed in a pumping cassette that is driven by the pump.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1a is an isometric view of an occlusion sensor on a pump chassis, in accord with the present invention, and a disposable pumping cassette coupled to an IV line monitored by the occlusion sensor;

FIG. 3a is a cross-sectional view taken along section line 2—2 in FIG. 1a, of a middle portion of the pump chassis, showing the pumping cassette aligned with the longitudinal axis of the pump chassis;

FIG. 3b is a cross-sectional view taken along a section line 3—3 in FIG. 1b;

Figure 14:
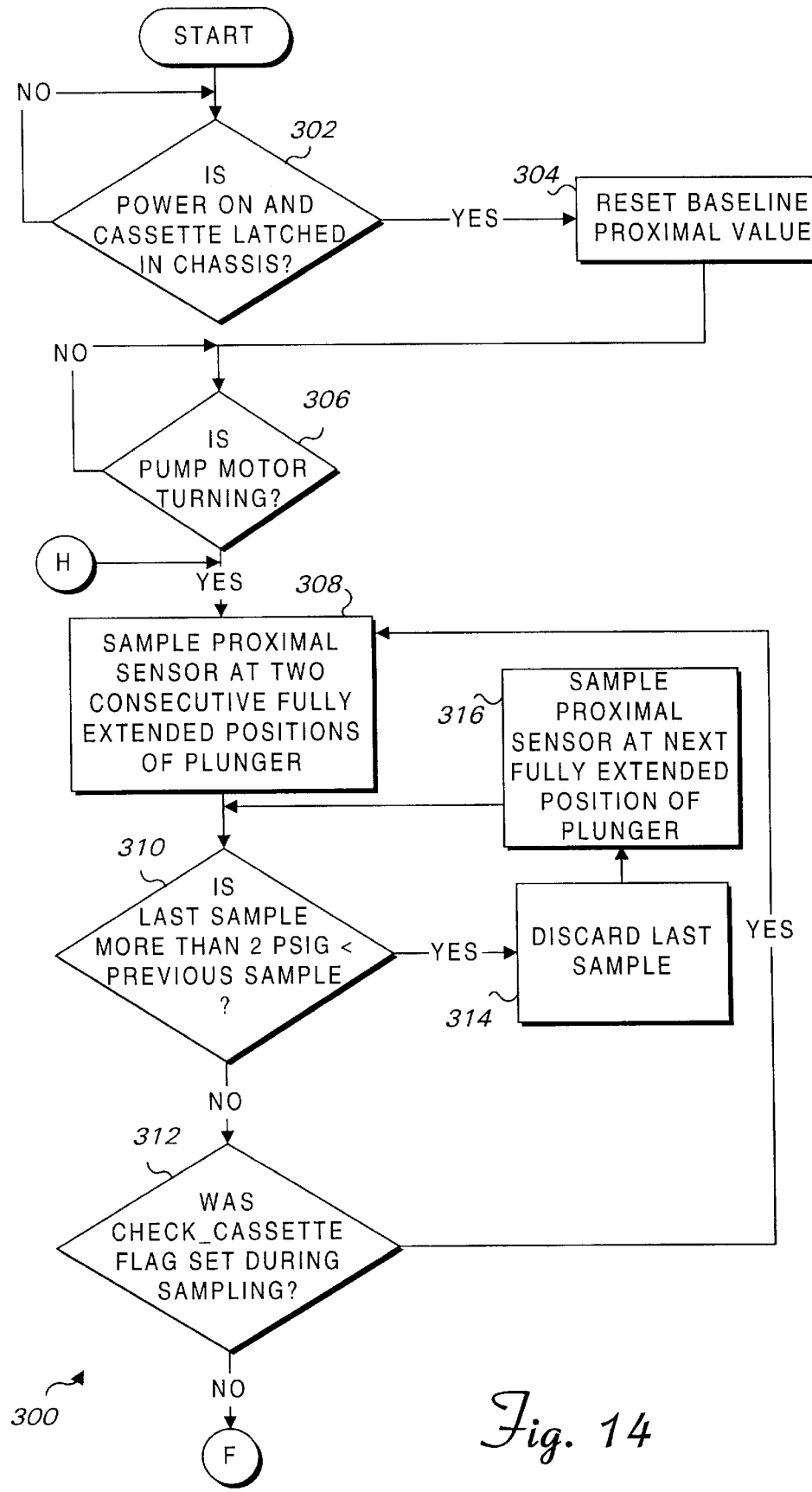
Figure 15:
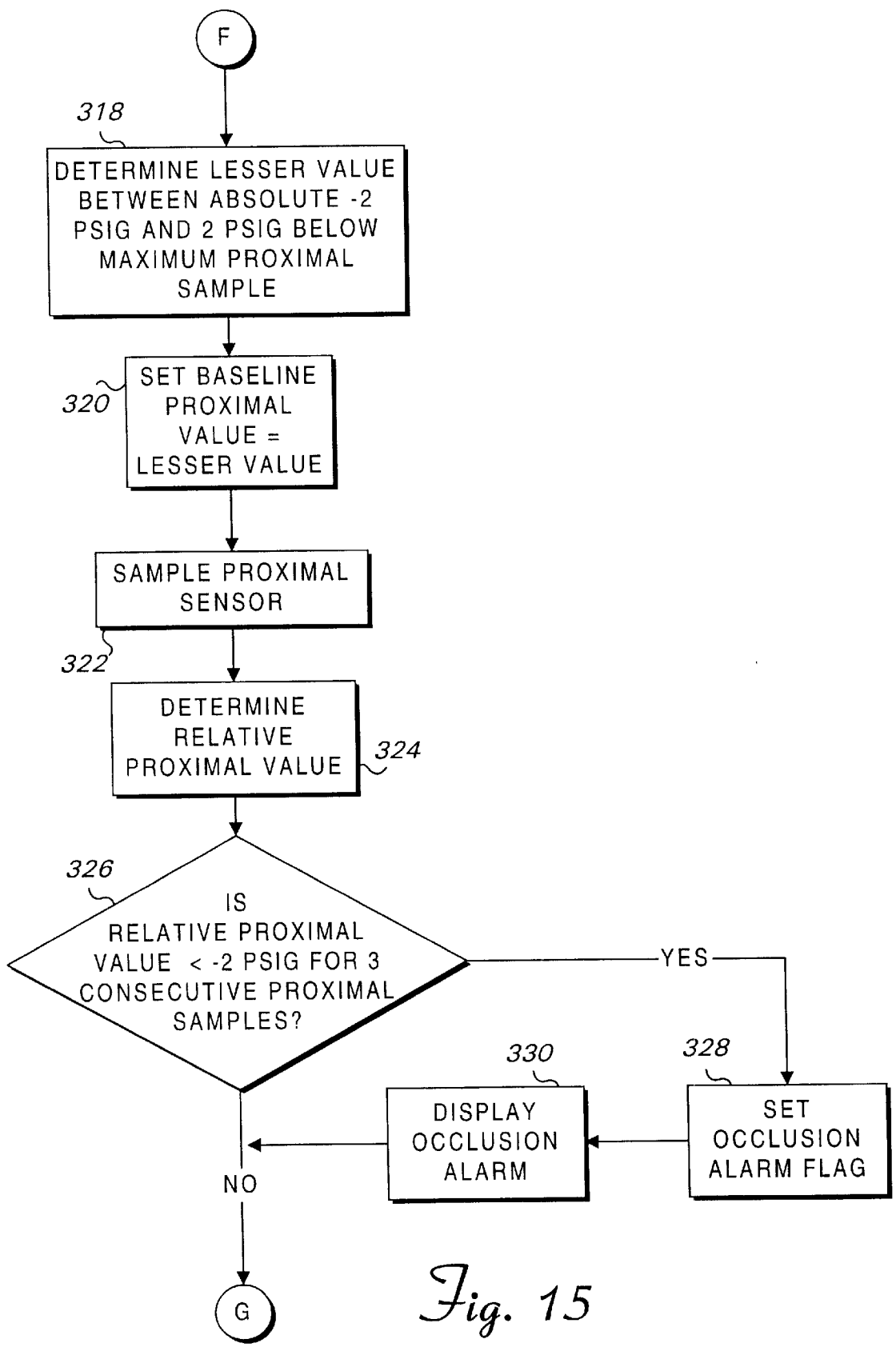
Figure 16:
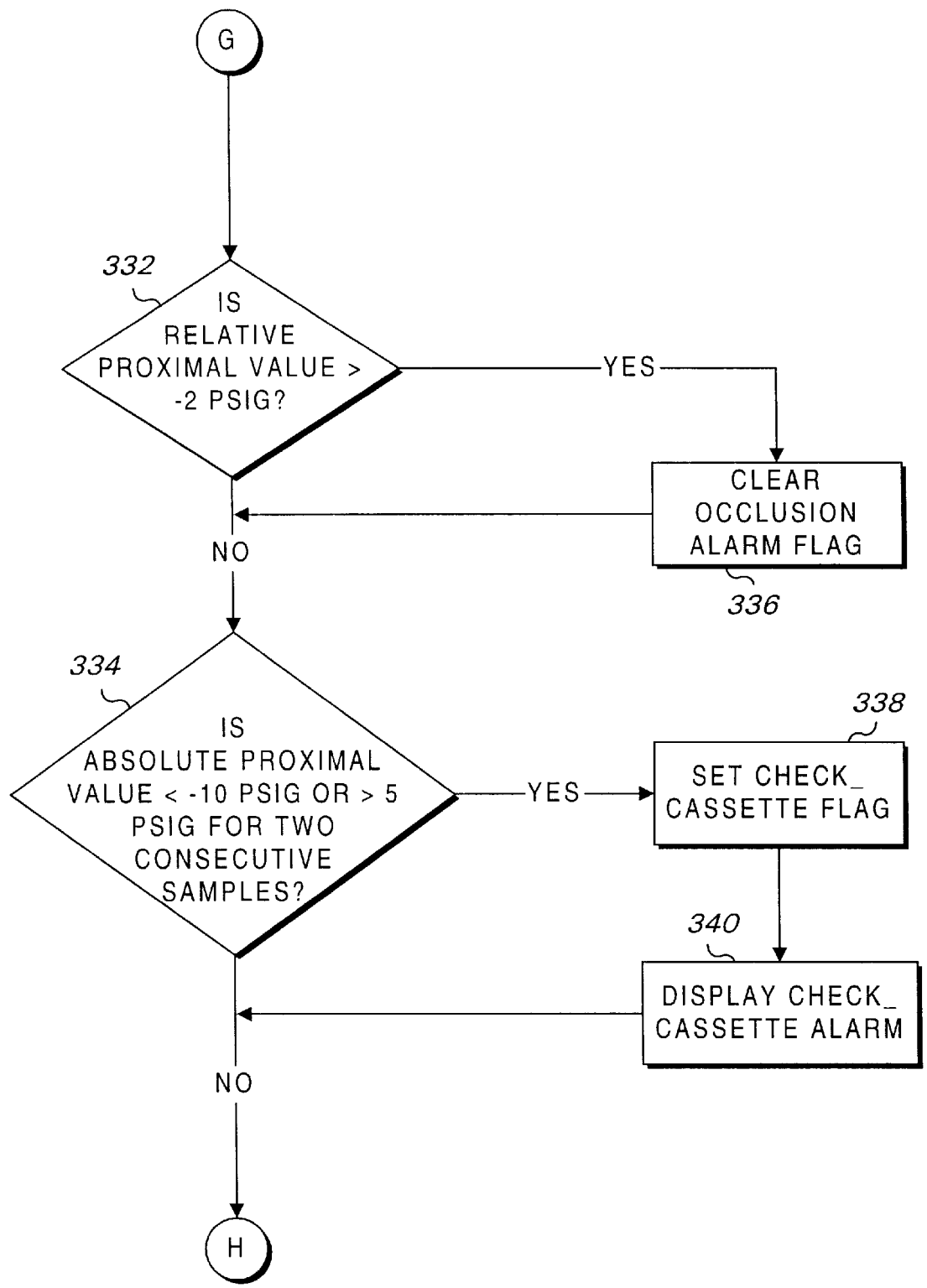

FIGS. 10, 11, 12, and 13 are a flow chart showing the steps employed to detect a distal occlusion in the IV line;

FIGS. 14, 15, and 16 are a flow chart illustrating the steps employed to detect a proximal occlusion in the IV line; and FIG. 17 is a table listing equations used for determining pressure in the pumping cassette.

DESCRIPTION OF THE PREFERRED EMBODIMENT

The strain gauge transducer produces a differential voltage corresponding to the amount of flex (pressure) on the beam by subjecting an array of four metal thin-film resistors to deformation. Typically, the strain gauge transducer is a complete assembly and each of the four metal resistors have an impedance of approximately 350 ohms per resistor.

FIG. 1a displays an intravenous pump assembly 100 that senses the distal pressure and the proximal pressure in a pumping cassette 114 in order to detect an impediment to the flow of liquid in an IV line comprising a proximal tubing 116 and a distal tubing 118. Pumping cassette 114, which includes an elastomeric membrane 120, a port 133 and a flow stop 122, is connected to the IV line between proximal tubing 116 and distal tubing 118. A tang 142 disposed on the lower portion of the pumping cassette, at its distal end, facilitates positioning and guiding distal tubing 118 into a slot 126. Slot 126 is disposed at the distal end of a pump chassis 112, and the pumping cassette is inserted in the slot and engaged by the pump chassis.

The interior of pump chassis 112 is adapted to engage pumping cassette 114 and position a reciprocating plunger 124 against the surface of elastomeric membrane 120, a rod 106a against the surface of flow stop 122, and a rod 106b against the surface of another portion of the elastomeric membrane that is accessed through port 133. A prime mover or electric motor 136 is coupled to a linkage (not shown) that reciprocatively drives plunger 124 against elastomeric membrane 120 when the motor rotates a cam (not shown) that is coupled to the plunger.

A pair of latches 110b are positioned within a pair of ports 134b that are disposed in a side wall of pump chassis 112. Although not shown in this Figure, a similar pair of latches 110a are positioned within a pair of ports 134a that are disposed in an opposite side wall of pump chassis 112. When pumping cassette 114 is inserted into pump chassis 112, the pairs of latches 110a and 110b are fully extended from within respective ports 134a and 134b, so that the latches engage notches 132b, which are formed on the sides of pumping cassette 114, firmly holding the pumping cassette at a predetermined position within the pump chassis interior. Conversely, when pairs of latches 110a and 110b are retracted into their respective ports 134a and 134b, they disengage from pumping cassette 114, so that the pumping cassette may be removed from the interior of pump chassis 112.

An elongate shaped member 108a extends generally parallel to the longitudinal axis of pump chassis 112, on one side thereof, and latches 110a are disposed on an inwardly facing surface of the member. Member 108a is pivotally connected to pump chassis 112 by a pair of hinges 103a that are disposed at opposed ends of the member's bottom edge. Similarly, an elongate shaped member 108b extends generally parallel to the longitudinal axis of pump chassis 112, at an opposite side of pump chassis 112 from member 108a, and pair of latches 110b are disposed on an inwardly facing surface of member 108b, which is pivotally connected to the pump chassis by a pair of hinges (not shown).

Figure 1B:
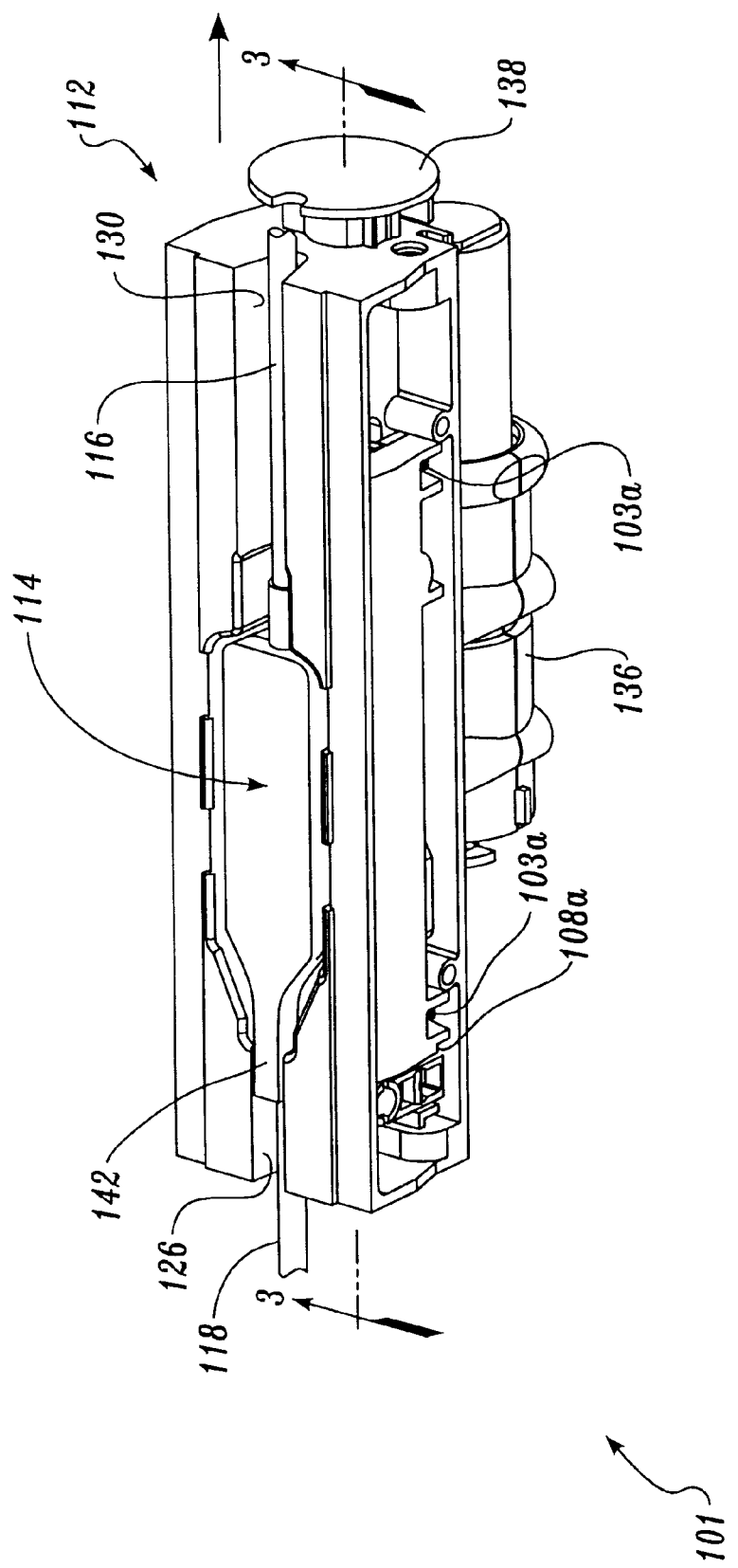
FIG. 1b is an isometric view of the occlusion sensor of FIG. 1a, showing the pumping cassette engaged by the IV pump chassis.

A linkage (not shown) is coupled to members 108a and 108b and to a user actuated plunger 138. User actuated plunger 138 is disposed at a proximal end of pump chassis 112. When the user actuated plunger is depressed in the direction of the arrow, as shown in FIG. 1a, the linkage to which it is coupled causes members 108a and 108b to pivot about their respective hinges, outwardly and away from the interior of the pump chassis, at both sides. When members 108a and 108b pivot outwardly in this manner, latches 110a and 110b move (retract) through ports 134a and 134b, so that the latches are not extended into the interior of pump chassis 112. When pumping cassette 114 is inserted into the interior of pump chassis 112, user actuated plunger 138 moves outwardly of the proximal end of pump chassis 112, and members 108a and 108b pivot about their respective hinges towards the interior of the pump chassis. This pivoting by members 108a and 108b causes latches 110a and 110b to be moved (extended) through ports 134a and 134b and into engagement with the pumping cassette. Latches 110a and 110b then engage notches 132a and 132b, which are formed on the opposite sides of the pumping cassette, and hold the cassette at a predetermined position, as shown in FIG. 1b. The linkage moves user actuated plunger 138 to the default position, which is shown in FIG. 1b.

In FIG. 1b, pumping cassette 114 is disposed in the interior of pump chassis 112 at the predetermined position. Members 108a and 108b are shown in the position in which the pumping cassette is engaged. Tang 142 is disposed within slot 126 and distal tubing 118 is positioned between ports 128a and 128b in the slot. Although not illustrated in this view, membrane 120 is in contact with plunger 124, so that reciprocation of the plunger forces medicinal liquid to flow through the pumping cassette when motor 136 is energized. Further, rod 106b is in contact with the portion of elastomeric membrane 120 that is accessed through port 133 and rod 106a is in contact with flow stop 122, which rides on top of another portion of the elastomeric membrane. When pumping cassette 114 is thus coupled to the pump chassis, very small distal and proximal pressures within the pumping cassette are transmitted through elastomeric membrane 120 and coupled to rods 106a and 106b.

Figure 2:
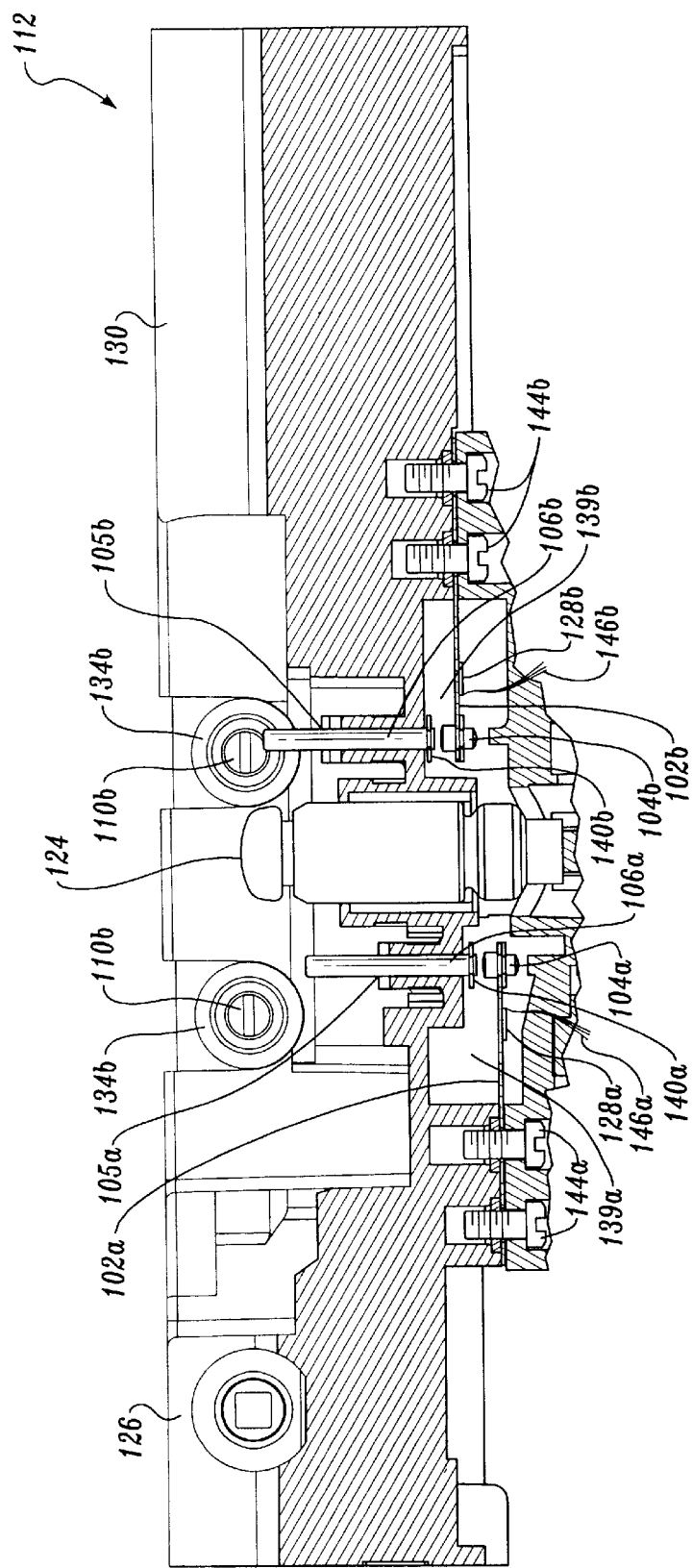
FIG. 2 is a cross-sectional view taken along a section line 2—2 in FIG. 1a, which extends along a longitudinal axis of the pump chassis.

Referring to FIG. 2, slot 130 is shown the proximal end of pump chassis 112 and slot 126 at the distal end of the pump chassis. Plunger 124 is positioned transversely to the interior of pump chassis 112, and pair of latches 110b are disposed inside the pair of ports 134b. Rod 106a is longitudinally disposed in a bore 105a that connects the interior of chassis 112 to a cavity 139a. Rod 106a is free to move in bore 105a, with one end of the rod disposed in the chassis interior and the other end disposed in cavity 139a. A keeper 140a is connected to the other end of rod 106a to prevent the rod falling through bore 105a into the interior of chassis 112.

A leaf spring 102a is disposed transverse to rod 106a in cavity 139a. An end portion of leaf spring 102a is fixed to pump chassis 112 by a pair of threaded fasteners 144a. A free end of leaf spring 102a is cantilevered from pump chassis 112 and free to flex in a direction responsive to longitudinal movement of rod 106a. A rounded knob 104a is connected to the free end of leaf spring 102a at a position that is directly opposite the adjacent end of rod 106a. A strain gauge 128a is mounted on leaf spring 102a, at a middle portion of the leaf spring between its free end and its mounted end. One end of a lead 146a is connected to strain gauge 128a and the other end is electrically connected to a controller 162 (not shown in this Figure). Lead 146a is employed to supply the excitation voltage for strain gauge 128a and convey a differential voltage to controller 162.

Similarly, a rod 106b is disposed in a bore 105b. An end of rod 106b is connected to a keeper 140b, which prevents the rod from slipping into the interior of the pump chassis through bore 105b. A leaf spring 102b is disposed in a cavity 139b and an end portion of the leaf spring is connected to pump chassis 112 by a pair of threaded fasteners 144b. A free end of leaf spring 102b is cantilevered from the pump chassis and is free to flex in a direction responsive to longitudinal movement of rod 106b. A rounded knob 104b is connected to the free end of the leaf spring, at a position opposite the adjacent end of rod 106b. A strain gauge 128b is mounted on a middle portion of leaf spring 102b, between its free end and its mounted end, and a lead 146b extends between the strain gauge and controller 162 (not shown here).

FIG. 3a depicts pumping cassette 114 (in phantom view) positioned adjacent to pump chassis 112, prior to engagement of the pumping cassette in the interior of the pump chassis. This Figure also shows how flow stop 122, elastomeric membrane 120, and elastomeric membrane 133 are aligned with rod 106a, plunger 124, and rod 106b, respectively. Flow stop 122 is illustrated in a closed position that disables free flow of a liquid through pumping cassette 114. The pairs of latches 110a and 110b are retracted within the pairs of ports 134a and 134b that are disposed in the side walls of pump chassis 112. It is important to note that the other ends of rods 106a and 106b are not preloaded (pressed) against the surface of knobs 104a and 104b, respectively. Further, the free ends of leaf springs 102a and 102b are disposed opposite and extend substantially normal to rods 106a and 106b, respectively.

FIG. 3b illustrates pumping cassette 114 engaged in pump chassis 112 and shows how flow stop 122, elastomeric membrane 120, and the portion of the elastomeric membrane accessed through port 133 are engaged by rod 106a, plunger 124, and rod 106b, respectively. Fluid pressure developed by plunger acting on the elastomeric membrane of pumping cassette 114 causes the flow stop to move to an open position, enabling the flow of liquid through the pumping cassette.

When pumping cassette 114 is engaged within the pump chassis, members 108a and 108b are in contact with the opposite sides of the pumping cassette, and latches 110a and 110b engage notches 132a and 132b, which are formed on the opposite sides of the pumping cassette, so that the cassette is held at the predetermined position within the pump chassis interior. The end of rod 106a is in contact with knob 104a and applies a preload force that flexes the free end of leaf spring 102a towards the interior of cavity 139a. Similarly, the end of rod 106b is in contact with knob 104b and applies a preload force that flexes the free end of leaf spring 102b towards the interior of cavity 139b. These preload forces stabilize the zero psig signal output from strain gauges 128a and 128b corresponding to a zero pressure level.

Figure 4:
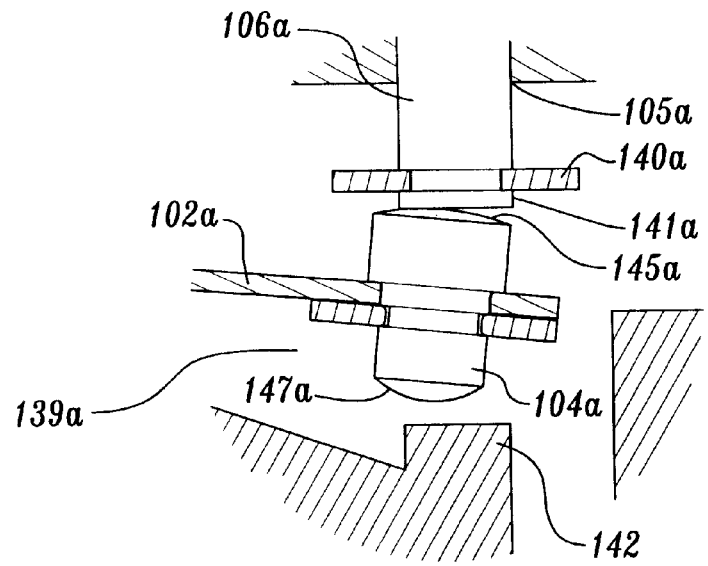
FIG. 4 is a cross-sectional view of an area 4 of FIG. 3b.

In FIG. 4, the end of rod 106a is shown extended from bore 105a towards the interior of cavity 139a. This end of rod 106a has a flat surface 141a that is pressed against a rounded surface 145a of knob 104a. Also, a rounded surface 147a is positioned adjacent, but apart from, a stop 143a, which limits the flexure travel of the free end of leaf spring 102a inside cavity 139a. The curvature of rounded surface 145a is provided to ensure that only normal forces are transmitted from rod 106a to leaf spring 102a. To further reduce the transmission of non-normal forces to leaf spring 102a, knob 104a is fabricated of a material that has an extremely low coefficient of friction such as DELRIN™ plastic. Also, rod 106a is preferably fabricated of an alloy impregnated or coated with TEFLON™ plastic to reduce friction within bore 105a, and between flat surface 141a and rounded surface 145a. It is desirable to only flex leaf spring 102a due to application of a normal force so that the differential voltage produced by strain gauge 128a more accurately reflects the actual pressure mechanically transmitted through the end of rod 106a in contact with flow stop 122.

Figure 5:
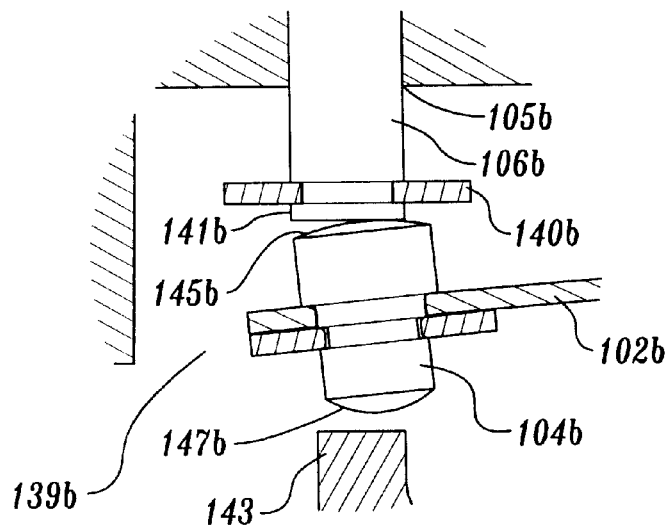
FIG. 5 is a cross-sectional view of an area 5 in FIG. 3b.

FIG. 5 illustrates how the end of rod 106b extends from bore 105b into cavity 139b so that a flat surface 141b on the rod contacts a rounded surface 145b on an end of knob 104b. A rounded surface 147b on the other end of the knob is adjacent, but spaced apart from a stop 143b, which serves to limit the flexure travel of the free end of leaf spring 102b within cavity 139b. The curve of rounded surface 145a minimizes transmission of non-normal force to leaf spring 102b. Also, as noted above in regard to knob 104a and rod 106a, knob 104b and rod 106b are fabricated of materials that have a low coefficient of friction to reduce friction and minimize the transmission of non-normal forces. The deflection of leaf spring 102b causes strain gauge 128b to produce a differential voltage that is indicative of the force applied to the end of rod 106b, which is in contact with the portion of elastomeric membrane 120 that is accessed through port 133, and is thus indicative of the pressure of the fluid acting on the opposite surface of the elastomeric membrane. Similarly, the deflection of leaf spring 102a causes strain gauge 128a to produce a differential voltage that is indicative of the force applied to the end of rod 106a through flow stop 122, which is in contact with the portion of elastomeric membrane 120 that underlies the flow stop; this force is thus indicative of the pressure of the fluid acting on the opposite surface of this portion of the elastomeric membrane.

Figure 6:
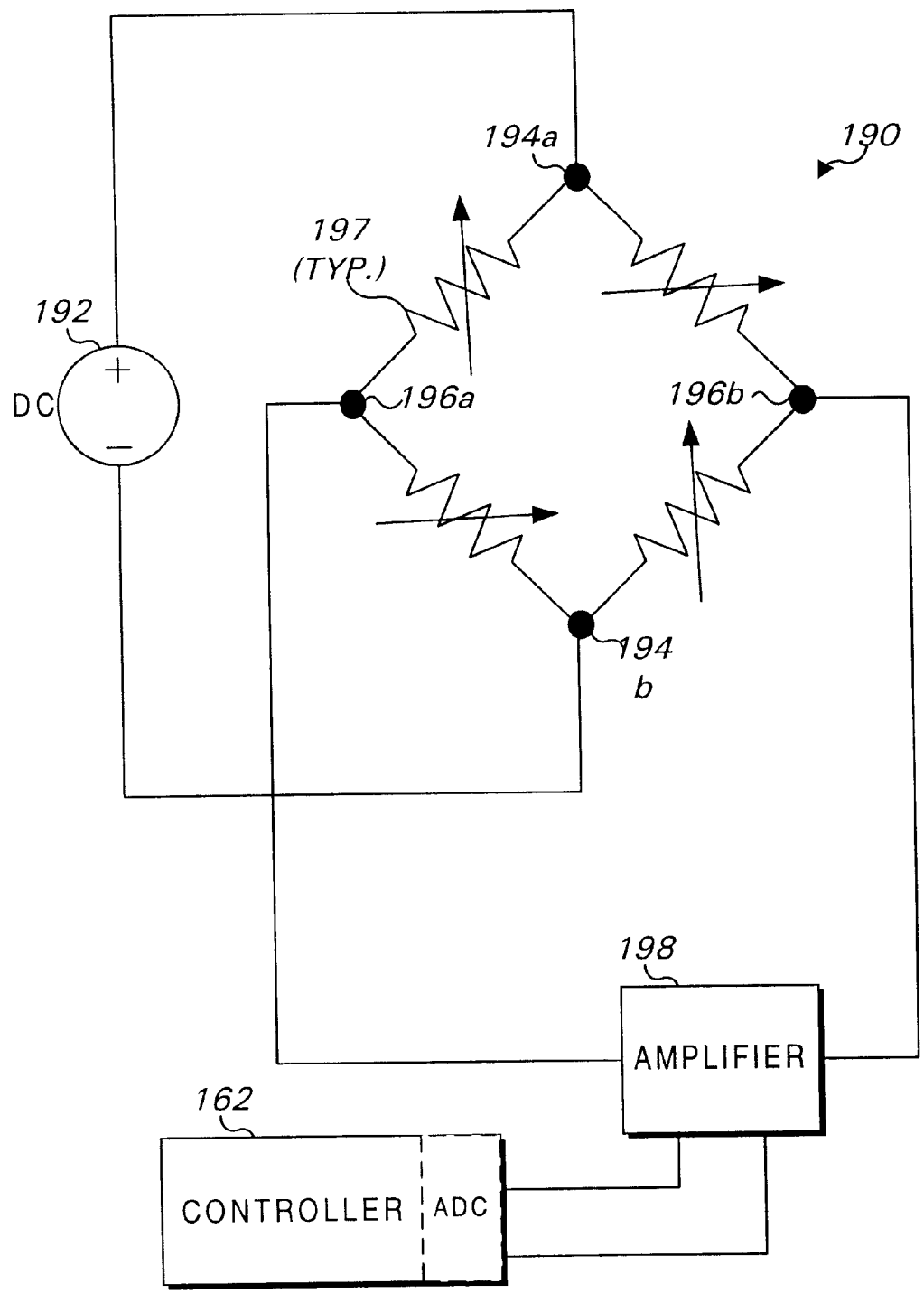
FIG. 6 is an electrical schematic diagram of a Wheatstone bridge circuit employed by the occlusion sensor.

In FIG. 6, a strain gauge 190 is illustrated, which is exemplary of a metal film resistor type that may be employed for strain gauges 128a and 128b. Strain gauge 190 includes an array of resistors 197 that are configured in a Wheatstone bridge circuit. A direct current (DC) supply 192 produces an excitation voltage that is applied to terminals 194a and 194b of the Wheatstone bridge. The resistance of at least one of resistors 197 varies with the stress applied thereto. The effect of varying the resistance of one or more of resistors 197 is to produce an imbalance in the Wheatstone bridge that causes a differential voltage across terminals 196a and 196b. This differential voltage is input to an amplifier 198 and amplified before it is supplied to controller 162.

Recently, semiconductor strain gauges have been developed that produce differential voltages ten times higher than those that use metal film resistors. Each leg of a semiconductor strain gauge bridge has an impedance that is a few thousand ohms and a current source is often used for excitation rather than a voltage source, to minimize temperature sensitivities. Although either type of strain gauge may be used with the present invention, a preferred embodiment uses a semiconductor strain gauge. As described in greater detail below, the present invention automates several of the calibration procedure steps for the output signal (differential voltage) produced by the semiconductor strain gauge as well as the metal film resistor strain gauge.

Control System

Generally, the present invention monitors the proximal and distal fluid pressures inside pumping cassette 114 to detect an impediment to the flow of a liquid in the IV line in which the pumping cassette is installed. Port 133 provides access to a portion of elastomeric membrane 120 at the proximal side of pumping cassette 114. Proximal fluid pressure inside pumping cassette 114 exerts a force on the elastomeric membrane that is mechanically transmitted through rod 106b to leaf spring 102b and strain gauge 128b. The output signal of strain gauge 128b is amplified and applied to an analog to digital conversion (ADC) input of controller 162. Controller 162 employs the ADC input to provide a digital signal corresponding to the proximal fluid pressure inside pumping cassette 114. The distal fluid pressure inside pumping cassette 114 is similarly measured, except that rod 106a is in contact with flow stop 122 and through the flow stop, in contact with the portion of the elastomeric membrane of the pumping cassette exposed to the distal fluid pressure of the IV line. In all other regards, the distal pressure is sensed in the same manner as the proximal pressure. The present invention also automates the output calibration steps for the proximal and distal pressures.

Figure 7:
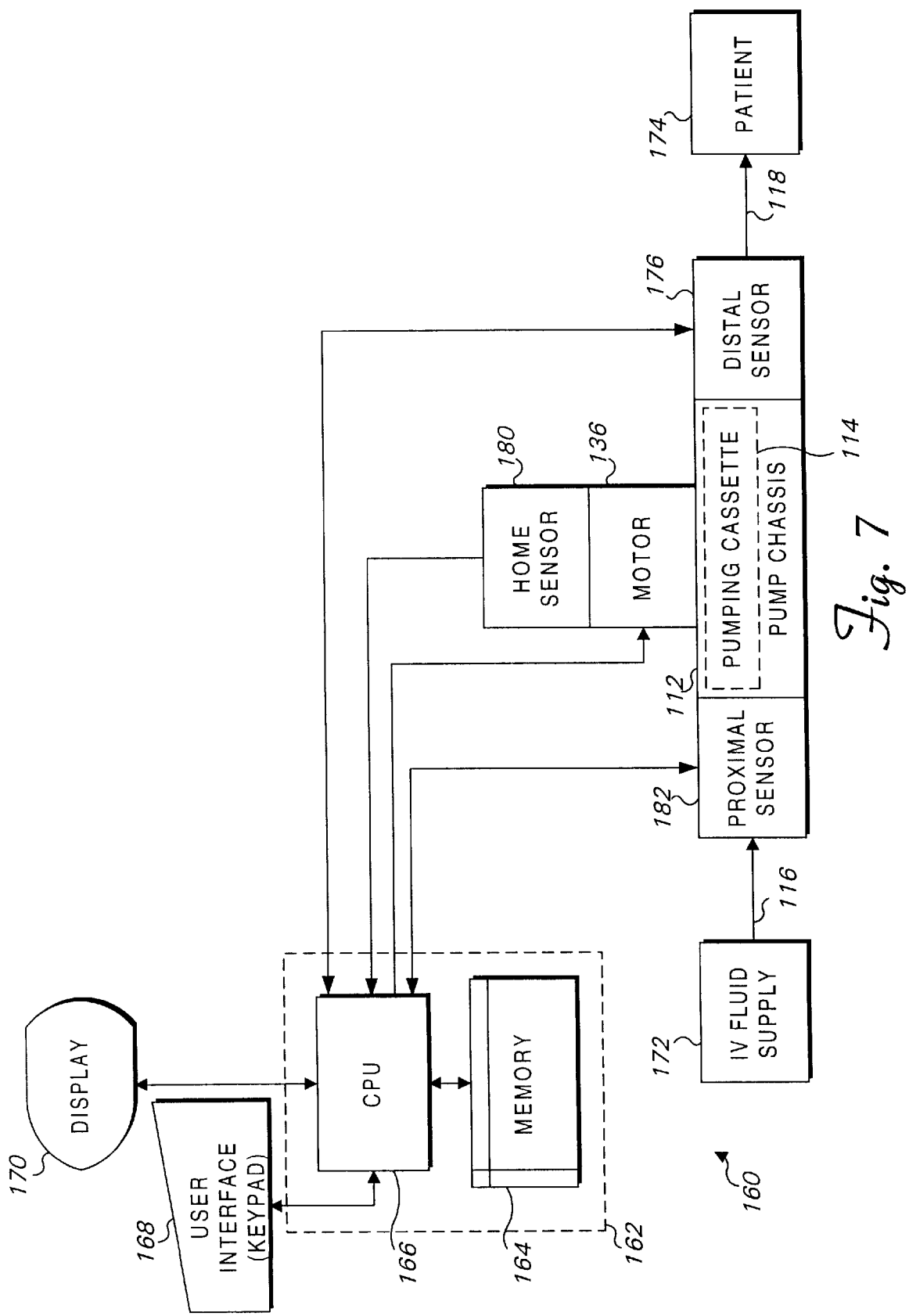
FIG. 7 is a functional block diagram that illustrates a control system for detecting an occlusion with a distal pressure sensor and a proximal pressure sensor.

In FIG. 7, an overview block diagram 160 of the medicinal fluid infusion system illustrates the control system for a proximal pressure sensor 182 and a distal pressure sensor 176. Proximal pressure sensor 182 and distal pressure sensor 176 include the components discussed above for producing output signals that are indicative of the respective proximal and distal pressures within pumping cassette 114. An intravenous medicinal liquid supply 172 is connected to proximal tubing 116 and supplies a medicinal liquid to pumping cassette 114, which is latched into pump chassis 112. Motor 136 is drivingly coupled to pumping cassette 114 so that the medicinal liquid may be administered to a patient 174 through distal tubing 118. A home position of a drive shaft (not shown) of motor 136 in the pumping cycle of pumping cassette 114 is detected by a home sensor 180 that is coupled to controller 162, which includes a central processing unit (CPU) 166 and a memory 164. Memory 164 stores a plurality of machine instructions that when executed by CPU 166, caused a plurality of functions to be implemented. Among the plurality of functions are the logical steps discussed below for calibration and monitoring proximal and distal pressures to detect a hindrance in the flow of the medicinal liquid through the IV line.

The system also includes a display 170 and a user interface 168, e.g., a keypad, which are connected to controller 162 to provide an interface for the user. In some IV systems, the IV pump may be coupled to a personal computer, so that the input device can include a mouse or other pointing device.

In one embodiment, home sensor 180 is an optical encoder coupled to the drive shaft of motor 136 for detecting a home position of the drive shaft. Typically, each pump stroke infuses 75 micro liters ($\mu l$) of liquid and is divided into 432 pulses (216 pulses for fill and 216 pulses for flow). The large number of pulses enables a high level of precision in delivery of the medicinal liquid and reduces the likelihood of needle clotting in the patient's body.

Power consumption of the IV pump is reduced by supplying power to proximal pressure sensor 182 and distal pressure sensor 176 only when motor 136 is energized. When controller 162 energizes proximal pressure sensor 182 and distal pressure sensor 176, approximately 1.5 milliseconds of warm up time are required before the sensor signals may be sampled. Also, controller 162 periodically checks the sampled signal from proximal pressure sensor 182 for a false low during the delivery of the medicinal liquid to the patient, so that an empty medical liquid supply 172 may be quickly detected. Furthermore, the logic discussed in detail below reduces false occlusion alarms by comparing/averaging two or more sampled signals. In this way, signal samples taken during minor pumping irregularities and occasional signal spikes do not trigger a false occlusion alarm.

Controller 162 determines the sampling time interval (in seconds) for distal pressure sensor 176 and proximal pressure sensor 182 during continuous rotation of motor 136 using the ratio of 6.06/R (R=RPM of the motor's output drive shaft). However, there are high and low limits to the sampling time interval. For example, if pumping cassette 114 is pumping at a relatively high delivery pressure (e.g., 18 psig absolute), then controller 162 halves the computed sampling time interval. Further, if pumping cassette 114 is pumping at a substantially lower rate, so that the computed sampling time interval is greater than one second, the sampling time interval is set at one second. Also, if motor 136 is rotating intermittently, the sampling time interval will be set to 101 milliseconds, which is based on a value for R=60 RPM.

Ideally, the sampling time interval begins when valves (not shown) in pumping cassette 114 open and the interval ends when the valves close. However, if pumping cassette 114 is pumping more than 125 milliliters per hour (ml/hr) of medicinal fluid, controller 162 may not sample proximal pressure sensor 182 during the delivery stroke and distal pressure sensor 176 may not be sampled during the intake stroke. The disposition of the valves in pumping cassette 114 are inferred from the position of the drive shaft of motor 136, which is sensed by home sensor 180. The standard sampling rate is approximately four samples per delivery stroke (e.g., at 30 millisecond intervals when delivering fluid at 1000 ml/hr), which is often enough to enable motor 136 to be de-energized before achieving a pressure of 40 psig at the distal end of pumping cassette 114.

In FIG. 17, a table 201 lists equations employed by controller 162 to determine an occlusion in the IV line. A threshold_adc equation 203 is used to calculate an ADC value that is a function of a threshold pressure, a baseline pressure and a factory zero pressure. A threshold_adc equation 205 is employed to calculate the corresponding ADC value for any relative pressure value that is not one of the calibration values (e.g., 5 psig relative). A delta_counts equation 207 is used to calculate the ADC counts corresponding to any delta pressure. A relative_adc equation 209 converts a relative pressure to its corresponding ADC value. An adc equation 211 is employed to convert an absolute pressure value to its ADC value.

Figure 8:
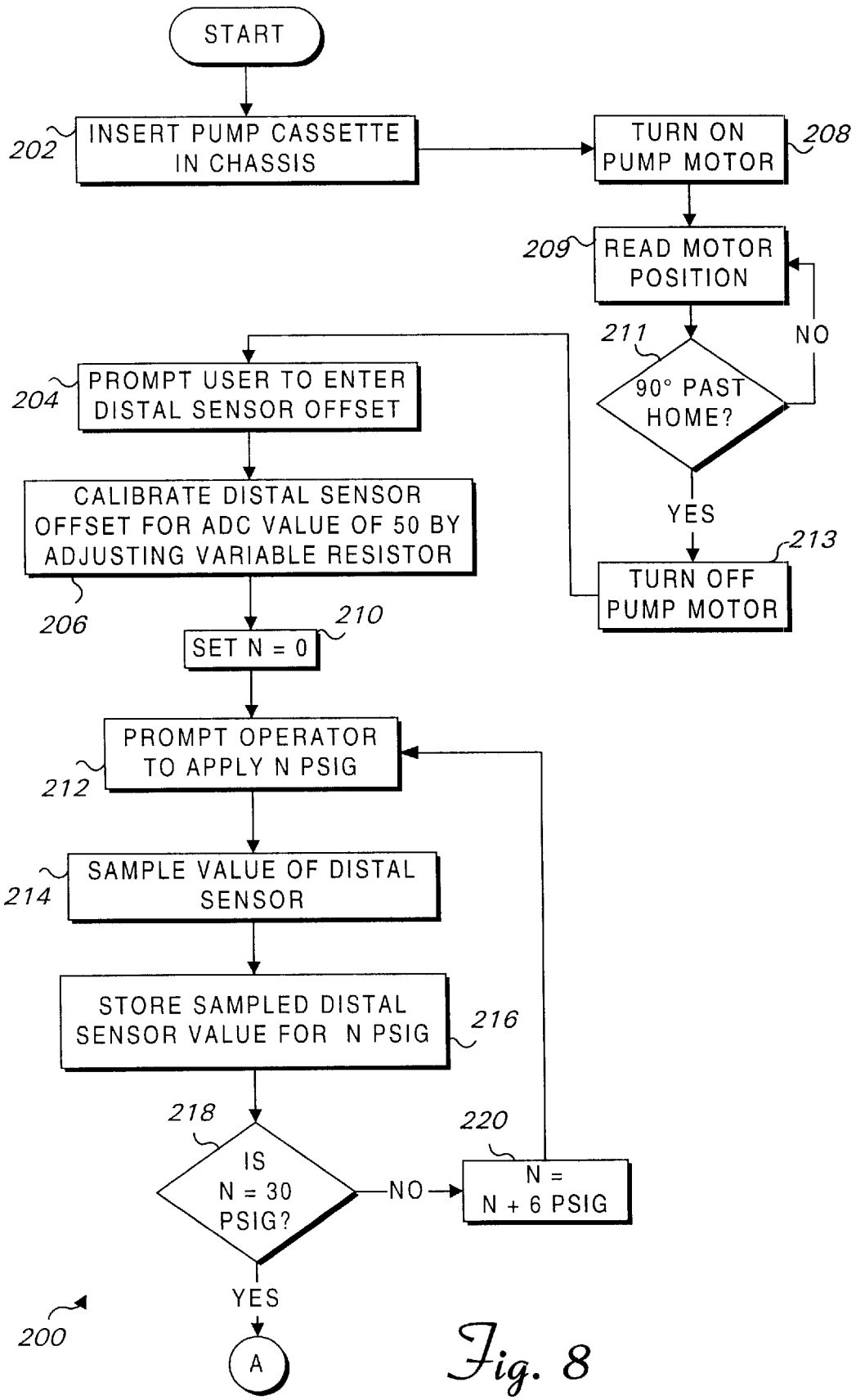
FIGS. 8 and 9 are a flow chart showing the steps employed to calibrate the distal pressure sensor and the proximal pressure sensor.
Figure 9:
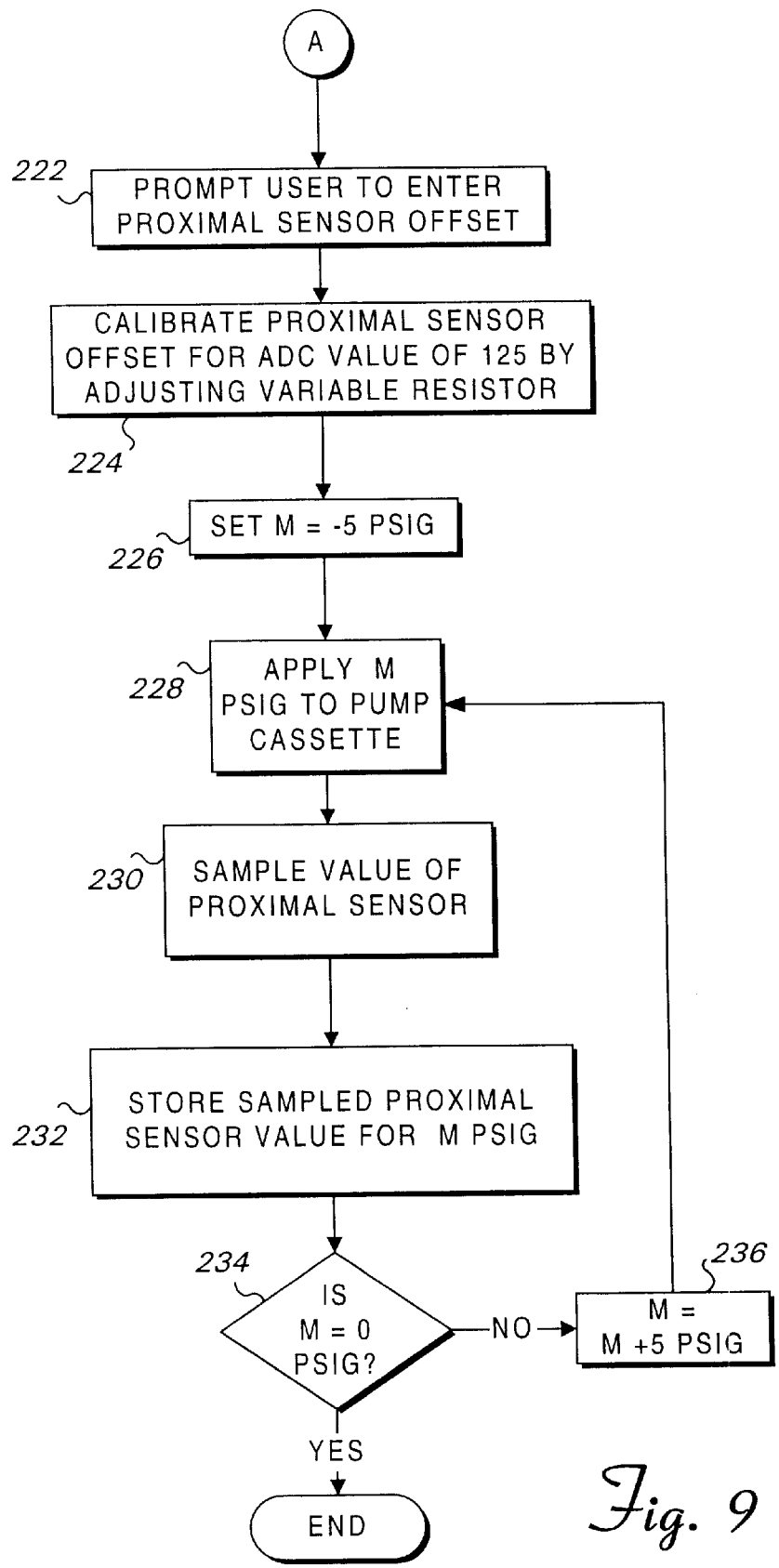

In FIGS. 8 and 9, an overview 200 illustrates the steps employed at the factory to calibrate distal pressure sensor 176 and proximal pressure sensor 182 before the pump chassis (in its housing—not shown) is shipped to the end user to be used for infusing a medicinal liquid into a patient. In FIGS. 8 and 9, the term "user" is intended to apply to the factory calibration operator—not the end user of the pump for medical applications. Also, in this and the other flow charts discussed below, it will be understood that the logical steps shown are implemented by CPU 166 in controller 162 when executing machine instructions that are stored in memory 164.

Moving from a start block, the logic steps to a block 202 in which pumping cassette 114 is inserted in pump chassis 112. At this point, the pump motor is turned on in a block 208, and the plunger is moved to a halfway extended position. To determine the plunger position, a block 209 provides for reading the position of the motor (shaft), and a decision block 211 loops until the motor position is 90° past its home position, which corresponds to the halfway extension of the plunger. Once this condition is achieved, a block 213 indicates that the pump motor is de-energized. At a block 204, the logic prompts a user to provide an offset value for distal pressure sensor 176. The logic proceeds to a block 206, which provides that the output of distal pressure sensor 176 is calibrated to an ADC value of 50. Controller 162 adjusts the impedance of an electronically variable resistor (not shown) to correspond to the offset value provided by the user. At a block 210, N is set equal to zero, and the logic advances to a block 212. A prompt is displayed to indicate that the user should apply N psig to the distal port of the pumping cassette to calibrate distal pressure sensor 176 (and press a control key on the keypad to indicate that the requested pressure has been applied to the distal pressure sensor). At a block 214, the output from distal pressure sensor 176 is sampled and monitored by the controller. In a block 216, the sampled distal sensor value for N psig is stored. At a decision block 218, a determination is made whether the current value of N is equal to 30. If not, the logic advances to a block 220 in which N is set equal to N plus six psig. The logic repeats this calibration sequence, returning to block 212 at each loop. When N is equal to 30 at decision block 218, the logic will have stored distal calibration threshold values of 0, 6, 12, 18, 24, and 30 psig.

If the determination at decision block 218 is true, the logic flows to a block 222 and the user is prompted to enter an eight bit offset value for proximal pressure sensor 182, as illustrated in FIG. 9. At a block 224, the output of proximal pressure sensor 182 is calibrated to an ADC value of 125 by the user adjusting the impedance of a variable resistor (not shown) to obtain a display of the user input offset value. At a block 226, M is set equal to −5 psig, and the logic flows to a block 228. The logic produces a prompt that indicates that pressure of M psig is to be applied by the user to the proximal port of the pumping cassette to be sensed by proximal pressure sensor 182. At a block 230, the output from proximal pressure sensor 182 is sampled at M psig. In a block 232, the reading of the output of proximal pressure sensor 182 is stored as a proximal calibration threshold value corresponding to the current value of M psig. At a decision block 234, a determination is made as to whether M is equal to 0. If false, the logic advances to a block 236 and M is set equal to M plus five psig. The logic then loops back to block 228, where the user is instructed to apply zero psig to the proximal port of the pumping cassette. The steps in blocks 230, 232, and decision block 234 are then repeated. At decision block 234, M will not equal zero, and the calibration procedure terminates. Proximal threshold calibration values corresponding to −5 and 0 psig will have been stored.

In FIGS. 10–13, an overview 290 includes the steps employed to detect an occlusion with distal pressure sensor 176. Note that any mention of "user" in regard to the description of FIGS. 10–15 refers to the end user of the invention, who is infusing a medicinal liquid into a patient.

Figure 10:
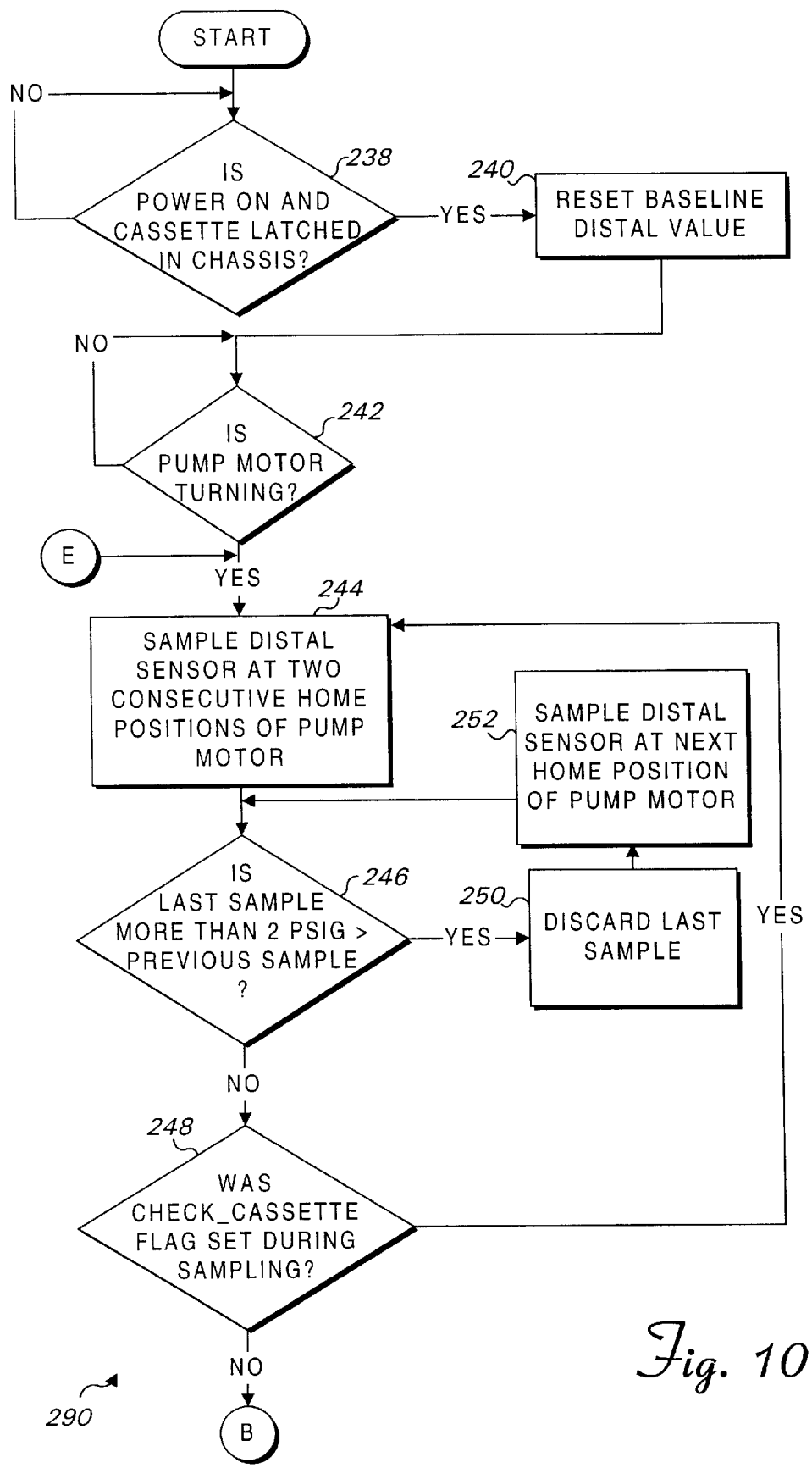
Figure 11:
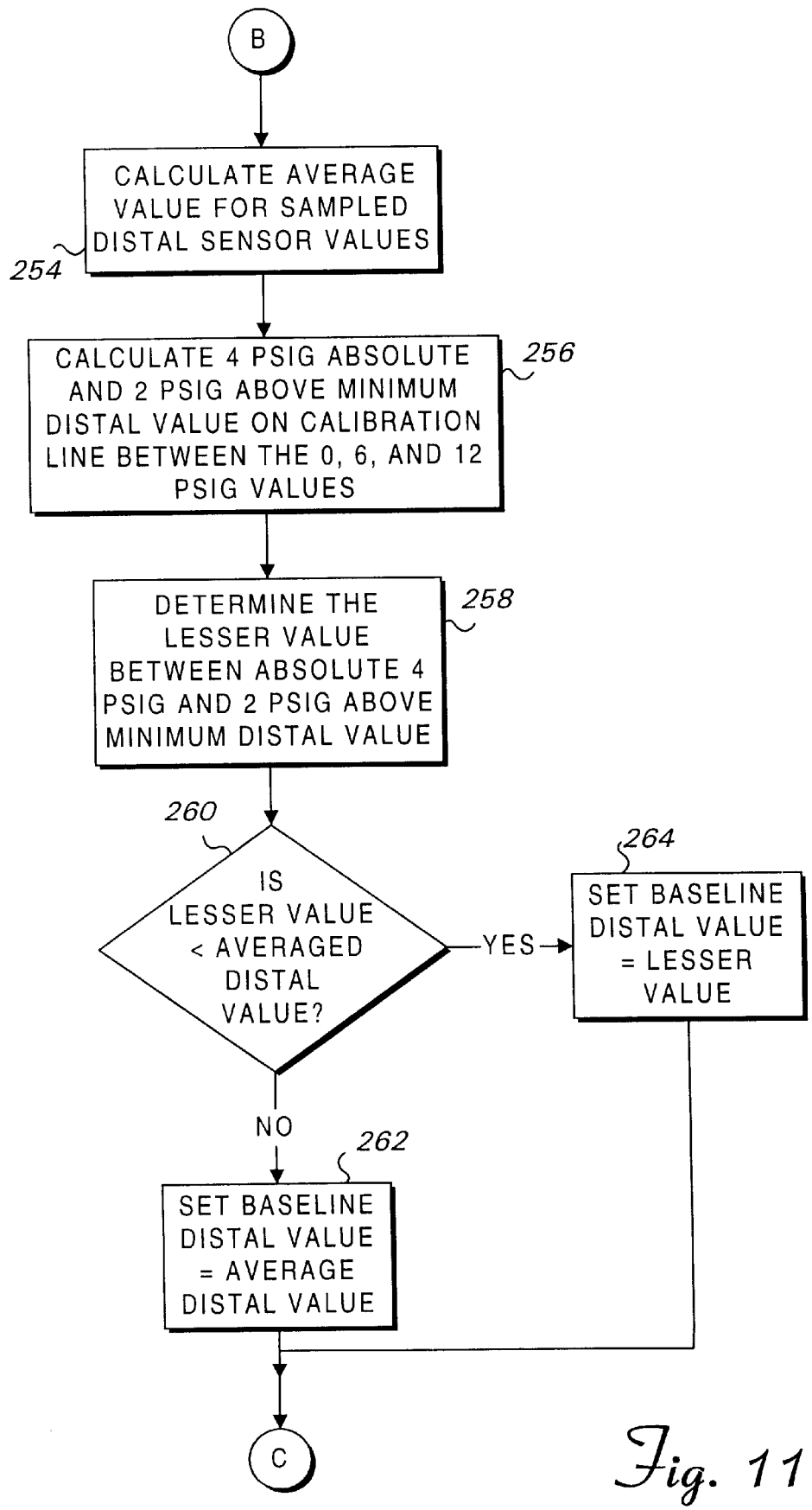

In FIG. 10, moving from a start block to a decision block 238, the logic determines if distal pressure sensor 176 is energized and pumping cassette 114 is latched in the predetermined position within the interior of pump chassis 112. The logic will loop until the determination is true and then advance to a block 240, in which a distal baseline value is reset (or set) equal to zero. The distal baseline value is calculated by averaging the two previous output signals that were sampled from distal pressure sensor 176 when the shaft (not shown) of motor 136 is in the home position. At a decision block 242, the logic determines if the shaft of motor 136 is rotating and loops until the determination is affirmative.

Next, in a block 244, two consecutive samples of the output signal from distal pressure sensor 176 are sampled. The logic at a decision block 246 determines if the last sample is more than 2 psig greater than the previous sample. If true, the logic flows to a block 250, and the last sample is discarded. In a block 252, the output signal for distal pressure sensor 176 is sampled at the next home position for the shaft of pump motor 136. The logic will continue looping back to decision block 246 until the last sample is within 2 psig of the previous sample being compared.

When the determination at decision block 246 is false, the logic advances to a decision block 248 to determine if a check_cassette flag was set during the two samplings of the output signal from distal pressure sensor 176. If true, the logic loops back to block 244, and two new consecutive samples of the output signal from distal pressure sensor 176 will be obtained. However, if the determination is false at decision block 248, the logic steps to a block 254 (FIG. 11) and calculates an average distal value for the last two consecutively sampled output signals from distal pressure sensor 176. At a block 256, the logic determines an absolute value of 4 psig and a value 2 psig above the lowest output signal sampled from distal pressure sensor 176 since pumping cassette 1 14 was latched into pump chassis 112. The 2 and 4 psig values are determined relative to a calibration line extending between the stored distal calibration threshold values for 0 and 12 psig.

At a block 258, the logic determines the lesser value of the 4 psig absolute value and the other value determined in block 256. A decision block 260 determines if the lesser value is less than the averaged distal value determined in block 254. If affirmative, the distal baseline value is set equal to the lesser value, and the logic advances to a block 266 (in FIG. 12). If the determination at decision block 260 is negative, the logic moves to a block 262, and the distal baseline value is set equal to the averaged distal value.

Figure 12:
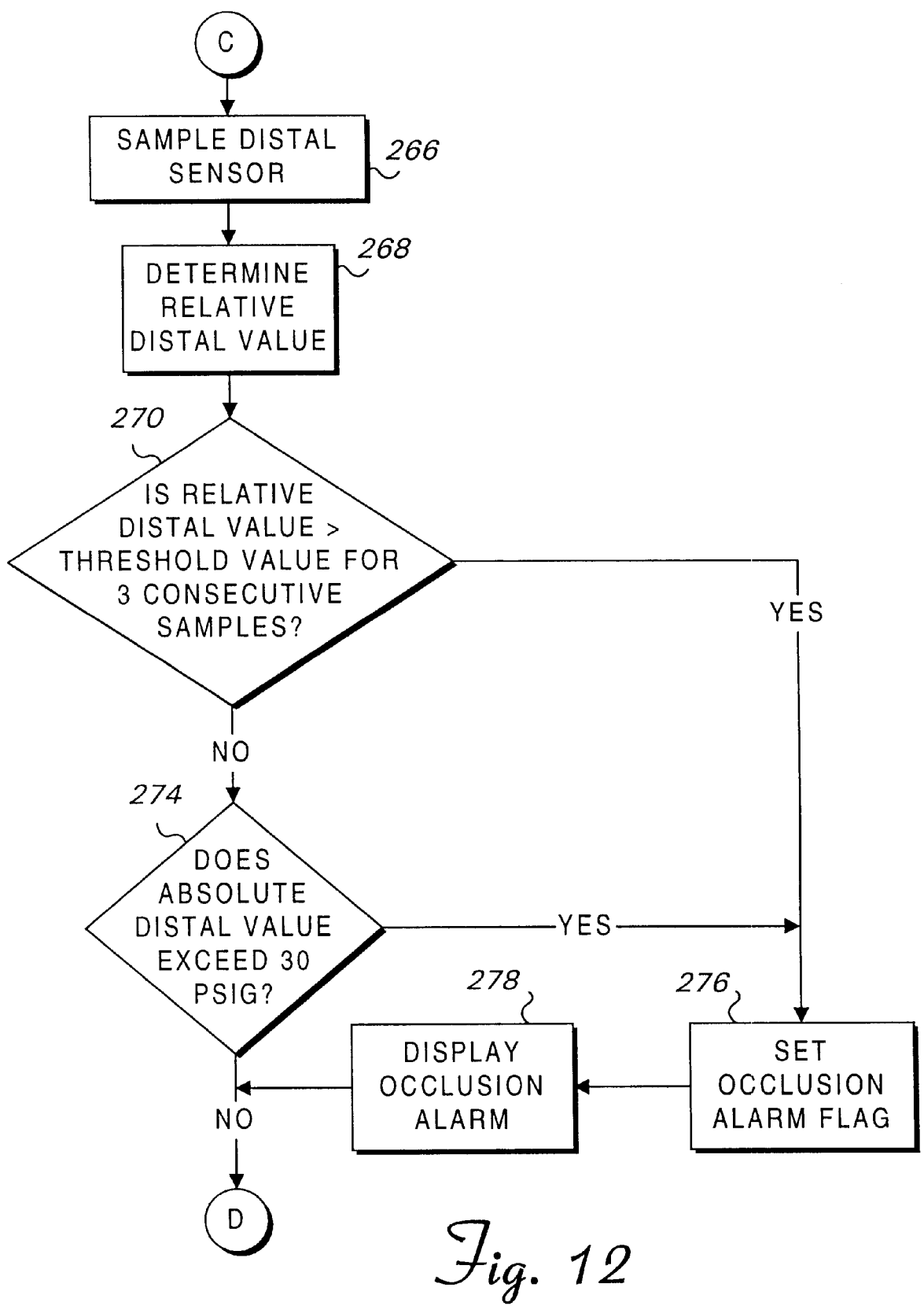
Figure 13:
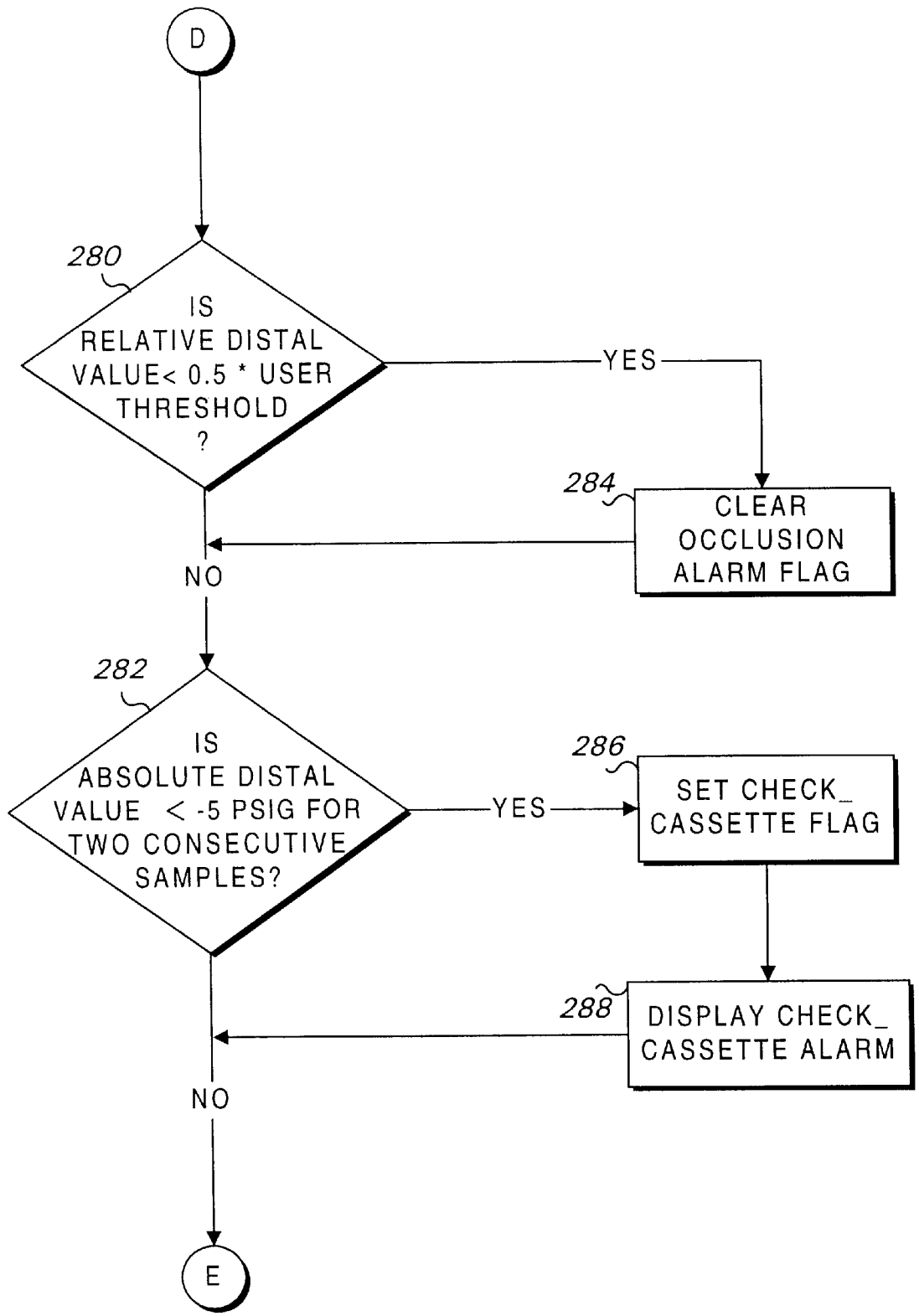

At block 266 in FIG. 12, the output signal from distal pressure sensor 176 is sampled. In a block 268, the equations that are illustrated in FIG. 17 are employed for calculating the relative distal pressure value. The user can select one of three sensitivities to be applied when detecting a distal occlusion alarm, corresponding to a HIGH, MEDIUM, and LOW pressure. The LOW distal pressure selection provides for a threshold of 6 psig, with a tolerance of ±3 psig. The MEDIUM distal pressure selection provides for a threshold of 12 psig, with a tolerance of ±5 psig. And, the HIGH distal pressure selection provides for a threshold of 24 psig, with a tolerance of ±5 psig.

A decision block 270 determines whether the relative distal pressure value for three consecutive samplings are each greater than the threshold value for the selected sensitivity range. If true, the logic steps to a block 276, and an occlusion alarm flag is set on. At a block 278, the occlusion alarm is displayed to the user, and the logic steps to a decision block 280 (in FIG. 13). However, if at decision block 270, the determination was false, the logic advances to a decision block 274 to determine if the absolute value of the distal pressure signal exceeds 30 psig. If affirmative, the logic flows back to block 276, and if negative, the logic proceeds to decision block 280 in FIG. 13.

At decision block 280, a determination is made as to whether the relative distal pressure value is less than one-half the user selected value for the threshold indicating an occlusion. If true, the logic flows to a block 284, and the occlusion alarm flag is set off or cleared. Thereafter, or if the result of decision block 280 is negative, the logic steps to a decision block 282, in which it is determined if the absolute distal pressure is less than −5 psig for two consecutive samples of distal pressure sensor 176, which is a condition that might indicate the pumping cassette has been removed from the pump chassis. If true, the logic advances to a block 286 in which the check_cassette flag is set on. At a block 288, the check_cassette alarm is displayed to the user. The logic returns to block 244 (in FIG. 10) from block 288 and also returns to block 244 if the determination at decision block 282 was false.

FIGS. 14–16 show an overview 300 of the steps employed to detect an occlusion with proximal pressure sensor 182. Moving from a start block to a decision block 302 in FIG. 14, the logic determines if proximal pressure sensor 182 is energized and pumping cassette 114 is latched in the predetermined position within pump chassis 112. The logic continues in a loop at decision block 302 until the determination is true and then advances to a block 304. This block provides for resetting (or setting) a proximal baseline value equal to zero. The proximal baseline value is the average of the two prior output signals from proximal pressure sensor 182 that have been sampled when the shaft (not shown) of pump motor 136 is in the position corresponding to the full extension of the plunger. At a decision block 306, the logic determines if the shaft of motor 136 is rotating and loops until the determination at decision block 306 is affirmative.

At a block 308, two consecutive samples of the output signal from proximal pressure sensor 182 are sampled (with the plunger fully extended). The logic at a decision block 310 then determines whether last sample from proximal pressure sensor 182 is more than 2 psig lower than the previous sample. If affirmative, the logic flows to a block 314 and the last sample is discarded. Advancing to a block 316, the output signal for proximal pressure sensor 182 is sampled at the next position for the shaft of pump motor 136 at which the plunger is fully extended. The logic continues looping back to decision block 310 until two samples are obtained that are within 2 psig of each other.

When the determination at decision block 310 is false, the logic advances to a decision block 312 to determine if the check_cassette flag was set during the sampling of the output signal from proximal pressure sensor 182. If affirmative, the logic loops back to block 308, so that two new consecutive samples are obtained from proximal pressure sensor 182. However, if the determination is negative at decision block 312, the logic advances to a block 318 (FIG. 15) in which the lesser of an absolute value of −2 psig and a value that is 2 psig below the highest output signal sampled from proximal pressure sensor 182 since pumping cassette 114 was latched into pump chassis 112 is determined. These −2 and 2 psig values are determined relative to a calibration line that extends between the stored proximal calibration threshold value for −5 psig and 0 psig. The logic moves to a block 320 in which the proximal baseline value is set equal to the sample that has the lesser value identified in block 318.

At a block 322, the output signal from proximal pressure sensor 182 is sampled and the logic steps to a block 324. The logic then employs the equations described in FIG. 17 to calculate the relative proximal pressure value. In a decision block 326, the logic decides whether the relative proximal pressure values for three consecutive samplings are all greater than the threshold value (relative to a calibration line produced with the stored proximal calibration threshold values). The allowed tolerance for this determination in the preferred embodiment is ±3 psig. If true, a block 328 indicates that the occlusion flag is set on. Next, the occlusion alarm is displayed to the user in a block 330.

Following a negative response to decision block 326 or after block 330, the logic advances to a decision block 332, as shown in FIG. 16. This decision block determines if the relative proximal pressure value is greater than −2 psig, and if so, the logic jumps to a block 336 in which the occlusion flag is set off or cleared. The logic next advances to a decision block 334 from block 336 or if the determination at decision block 332 is false. Decision block 334 determines if the absolute proximal pressure values for two consecutive samplings are less than −10 psig or greater than 5 psig, which may indicate that the pumping cassette has been removed. If true, the logic advances to a block 338 and the check_cassette flag is set on. At a block 340, the check_cassette alarm is displayed to the user. The logic returns to block 308 (in FIG. 14) from block 340 or if the determination at decision block 334 is false.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A system for detecting an impediment to a fluid flow through an intravenous line, comprising:

(a) a pump chassis;

(b) a pump in fluid communication with the intravenous line and mountable within the pump chassis to receive a driving force, said pump including a proximal port, a distal port, and an elastomeric membrane overlying a fluid path through the fluid pump adjacent the proximal port and distal port;

(c) a proximal pressure sensor mounted on the pump chassis and including a member that is coupled to the elastomeric membrane adjacent to the proximal port of the pump and responsive to a deflection and force exerted by the elastomeric membrane due to a proximal fluid pressure within the pump, producing a proximal pressure signal indicative thereof;

(d) a distal pressure sensor mounted on the pump chassis and including a member that is coupled to the elastomeric membrane adjacent to the distal port of the pump and responsive to a deflection and force exerted by the elastomeric membrane due to a distal fluid pressure within the pump, producing a distal pressure signal indicative thereof; and (e) a controller that is electrically coupled to the proximal pressure sensor and the distal pressure sensor to receive the proximal and distal pressure signals, said controller employing the proximal pressure signal to determine a baseline proximal pressure and an absolute proximal pressure, and employing the distal pressure signal to determine a baseline distal pressure and an absolute distal pressure, and determining whether an impediment to fluid flow through the intravenous line has occurred as a function of the baseline proximal pressure, the baseline distal pressure, the absolute proximal pressure, and the absolute distal pressure.

2. The system of claim 1, wherein the pump comprises a pumping cassette, the pump chassis latching the pumping cassette in a predetermined position within the pump chassis before the controller begins monitoring the proximal pressure and the distal pressure.

3. The system of claim 2, wherein latching the pumping cassette in the pump chassis applies a preload force from the elastomeric membrane directed against the proximal pressure sensor and against the distal pressure sensor through their respective members, said preload force tending to stabilize a zero proximal pressure signal and a zero distal pressure signal.

4. The system of claim 2, wherein the proximal pressure sensor and the distal pressure sensor each comprise:
   (a) a beam having an end rigidly connected to the pump chassis and a free end that flexes in response to a force applied by the member; and
   (b) a strain gauge mounted on the beam, said strain gauge responding to a flexure of the beam by producing an output signal indicative of one of the proximal and the distal pressures.

5. The system of claim 4, wherein the member of each of the proximal and distal pressure sensors comprises an elongate rod that is movable along a longitudinal axis of the rod within an orifice that is disposed in the pump chassis, in response to a force exerted by the fluid within the pumping cassette against the elastomeric membrane, said force being a function of a fluid pressure.

6. The system of claim 5, wherein each rod is impregnated with at least one material selected to substantially reduce friction between the rod and the orifice in the pump chassis through which the rod moves.

7. The system of claim 5, where each beam includes a knob mounted on the free end thereof, adjacent to an end of the rod, at least one of the end of the rod and an end of the knob that contacts the end of the rod including a surface having a curvature selected to isolate the beam from any forces by the rod that are not directed generally in parallel with the longitudinal axis of the rod.

8. The system of claim 7, wherein each knob is fabricated of a material selected because of its low coefficient of friction, to minimize an effect of forces applied to the knob by the rod that are not substantially normal to the beam.

9. The system of claim 7, wherein the rod of the distal pressure sensor contacts a flow stop disposed on the pumping cassette, the flow stop being disposed adjacent to and in contact with a portion of the elastomeric membrane within the pumping cassette.

10. The system of claim 9, wherein the flow stop is pivotally mounted on the pumping cassette to pivot between an open position in which the flow stop permits a flow of fluid through the pumping cassette and transmits a force from the elastomeric membrane to the rod of the distal pressure sensor that corresponds to the distal pressure, and a closed position in which the flow stop interrupts a free flow of the fluid through the pumping cassette, the rod of the distal pressure sensor automatically moving the flow stop to the open position when the pumping cassette is latched into the chassis.

11. The system of claim 1, wherein the controller comprises:
   (a) a processor;
   (b) user interface that permits entry of data by a user;
   (c) a display for displaying prompts and information to a user; and
   (d) a memory that is coupled to the processor, the memory storing a plurality machine instructions that cause the processor to perform a plurality of logical steps when the machine instructions are executed by the processor, said logical steps including:
      (i) enabling calibration of the proximal pressure sensor and the distal pressure sensor before the pump is initially placed into operation to pump the fluid, said calibration storing a proximal offset, a distal offset, and calibration threshold values for the proximal pressure sensor and the distal pressure sensor in the memory;
      (ii) when the pump is placed into operation to pump the fluid, sampling the proximal pressure signal produced by the proximal pressure sensor and the distal pressure signal produced by the distal pressure sensor to determine the baseline proximal pressure and the baseline distal pressure, respectively, using the proximal offset and the distal offset and the calibration threshold values; and
      (iii) producing an occlusion alarm on the display if samples of the proximal pressure signal or the distal pressure signal indicate that the impediment to the fluid flow has occurred.

12. The system of claim 11, wherein the controller further includes an analog-to-digital converter that converts the proximal pressure signal to a corresponding digital value and the distal pressure signal to a corresponding digital value.

13. A method for detecting an impediment to fluid flow through an intravenous line in which is disposed a pump for infusing a medicinal fluid into a patient, comprising the steps of:
   (a) sensing a fluid pressure in the pump, producing a fluid pressure signal;
   (b) sampling the fluid pressure signal a plurality of time, when the pump is at a predefined point in a pumping cycle, producing samples;
   (c) determining a baseline pressure;
   (d) detecting that an impediment to fluid flow has occurred as a function of the baseline pressure and a threshold value; and
   (e) providing an alarm to alert a user if the impediment to fluid flow is detected.

14. The method of claim 13, further comprising the step of providing a pressure calibration of a pressure sensor used to sense the fluid pressure in the pump before the pump is made available for use infusing the medicinal fluid into the patient.

15. The method of claim 13, wherein the step of sampling further comprises the steps of:
   (a) determining if the pump is energized; and if so,
   (b) determining if the pump is pumping the fluid; and if so,
   (c) enabling samples to be taken to determine the baseline pressure.

16. The method of claim 13, wherein the step of determining the baseline pressure comprises the steps of:
   (a) determining if a difference between the successive samples is within a predetermined limit; and if true
   (b) determining the average of the successive samples for use as the baseline pressure; but if false
   (c) discarding a last of the successive samples;

(d) taking another sample, which becomes the last sample; and (e) repeating the steps of this claim until the average for use as the baseline pressure is determined.

17. The method of claim 13, wherein the step of determining the baseline pressure comprises the steps of:

(a) determining a maximum value of the samples taken since the pump began to operate, while excluding any sample that differs by more than a predefined limit from a previous sample; and (b) limiting the baseline pressure to a value that is the greater of a predefined function of the maximum value, and a specified pressure value.

18. The method of claim 13, wherein the step of determining the baseline pressure comprises the steps of:

(a) determining a minimum value of the samples taken since the pump began to operate, while excluding any sample that differs by more than a predefined limit from a previous sample; and (b) limiting the baseline pressure to a value that is the lesser of a predefined function of the minimum value, and a specified pressure value.

19. The method of claim 13, wherein the step of determining the baseline pressure further comprises the step of eliminating any samples taken while the fluid pressure signal indicates that the pump is not operating, so that said samples are not used to determine the baseline pressure.

20. The method of claim 13, further comprising the steps of determining an operating speed of the pump and determining a rate for sampling the pressure signal as a function of said operating speed.

21. The method of claim 13, further comprising the step of detecting that an impediment to fluid flow has occurred as a function of an absolute pressure that is independent of the baseline pressure.

22. The method of claim 21, wherein the impediment to fluid flow is detected if a difference between the absolute pressure and a predetermined value is exceeded.

23. The method of claim 13, wherein the fluid pressure signal is indicative of one of a proximal pressure and a distal pressure in the intravenous line.

24. An occlusion detector disposed in a pump that infuses a medicinal fluid into a patient through an intravenous line, for determining if an impediment to fluid flow through the intravenous line has occurred, comprising:

(a) a beam that is cantilever mounted to the pump, so that a free end of the beam is able to flex in response to a force applied to the free end of the beam;

(b) a strain gauge mounted on the beam so as to sense a deflection of the beam;

(c) an elongate rod disposed within an orifice formed within the pump and movable in a direction aligned with a longitudinal axis of the rod, one end of the rod contacting the free end of the beam, an opposite end of the rod having a force corresponding to a fluid pressure within the intravenous line applied thereto, in the direction of the longitudinal axis of the rod, said force causing the beam to deflect and thus causing the strain gauge to produce a signal indicative of the fluid pressure;

(d) an alarm indicative of an impediment to fluid flow through the intravenous line; and (e) a controller coupled to the strain gauge to receive the signal, said controller sampling the signal to produce samples and to determine a baseline pressure while the pump is operating, and as a function of the baseline pressure, determining a relative pressure, said controller detecting an impediment to the fluid flow through the intravenous line as a function of the relative pressure and causing the alarm to be activated to alert a user of the impediment to the fluid flow.

25. The occlusion detector of claim 24, wherein the signal is indicative of one of a distal pressure and a proximal pressure in the intravenous line.

26. The occlusion detector of claim 24, wherein the rod is fabricated of a material selected for its low coefficient of friction, to minimize friction between the rod and sides of the orifice.

27. The occlusion detector of claim 24, wherein the free end of the beam includes a knob disposed adjacent to and in contact with the end of the rod, at least one of the end of the rod and a surface of the knob in contact with the end of the rod being rounded to minimize application of force by the rod on the beam that is not aligned with the longitudinal axis of the rod.

28. The occlusion detector of claim 24, wherein the baseline pressure is:

(a) reset each time the pump is energized; and (b) determined by averaging a plurality of samples that do not differ from each other by more than a predetermined amount.

29. The occlusion detector of claim 25, wherein the pump is adapted to drive a pumping cassette that includes an elastomeric membrane that is in contact with the medicinal fluid, said rod being adapted to receive the force from the elastomeric membrane in response to the pressure of the medicinal fluid flowing through the intravenous line.

30. The occlusion detector of claim 28, wherein the baseline pressure is limited to the greater of a predefined function of a maximum sample, and a predetermined value.

31. The occlusion detector of claim 28, wherein the baseline pressure is limited to the lesser of a predefined function of a minimum sample, and a predetermined value.

32. The occlusion detector of claim 28, wherein the controller detects an impediment to the fluid flow as a function of an absolute pressure derived from the samples and independent of the baseline pressure.

33. A system for detecting an impediment to a fluid flow through an intravenous line, comprising:

(a) a pump chassis;

(b) a pump in fluid communication with the intravenous line and mountable within the pump chassis to receive a driving force, said pump including a proximal port, a distal port, an elastomeric membrane overlying a fluid path through the fluid pump adjacent the proximal port and distal port, and a flow stop that is in contact with the elastomeric membrane adjacent to the distal port, said flow stop being movable between a stop position in which it applies a force to the elastomeric membrane that closes off fluid flow through the pump and a sensing position in which it transmits force produced by a distal pressure within the pump and thus, indicative of the distal pressure;

(c) a proximal pressure sensor mounted on the pump chassis and including a member that is coupled to the elastomeric membrane adjacent to the proximal port of the pump and responsive to a deflection and force exerted by the elastomeric membrane due to a proximal fluid pressure within the pump, producing a proximal pressure signal indicative thereof;

(d) a distal pressure sensor mounted on the pump chassis and coupled to the flow stop to respond to the force transmitted by the flow stop from the elastomeric membrane, producing a distal pressure signal indicative thereof; and (e) a controller that is electrically coupled to the proximal pressure sensor and the distal pressure sensor to receive the proximal and distal pressure signals, said controller employing the proximal pressure signal to determine a proximal fluid pressure, and employing the distal pressure signal to determine a distal fluid pressure, and determining whether an impediment to fluid flow through the intravenous line has occurred as a function of the proximal fluid pressure, and of the distal fluid pressure.

* * * * *